(12) United States Patent
Kania

(10) Patent No.: US 7,135,005 B2
(45) Date of Patent: Nov. 14, 2006

(54) SHOULDER BRACE

(75) Inventor: Bruce G. Kania, Bozeman, MT (US)

(73) Assignee: Fountainhead, LLC, Shepherd, MT (US)

( * ) Notice: Subject to any disclaimer, the term of this patent is extended or adjusted under 35 U.S.C. 154(b) by 28 days.

(21) Appl. No.: 10/204,077

(22) PCT Filed: Feb. 20, 2001

(86) PCT No.: PCT/US01/05300

§ 371 (c)(1),
(2), (4) Date: Oct. 7, 2002

(87) PCT Pub. No.: WO01/60291

PCT Pub. Date: Aug. 23, 2001

(65) Prior Publication Data

US 2003/0208146 A1    Nov. 6, 2003

(51) Int. Cl.
*A61F 5/00* (2006.01)

(52) U.S. Cl. .......................................... 602/19; 602/20

(58) Field of Classification Search .................... 602/4, 602/20, 24, 19, 60, 61, 62, 67; 128/98.1, 128/99.1, 878
See application file for complete search history.

(56) References Cited

U.S. PATENT DOCUMENTS

| | | | |
|---|---|---|---|
| 2,859,746 A | 11/1958 | Robertson | |
| 3,504,377 A | 4/1970 | Biggs, Jr., et al. | |
| 4,188,944 A | 2/1980 | Augustyniak | |
| 4,198,964 A * | 4/1980 | Honneffer | 602/19 |
| 4,327,909 A | 5/1982 | Neufeld | |
| 4,862,878 A | 9/1989 | Davison et al. | |
| 4,947,870 A | 8/1990 | Larcher | |
| 5,020,521 A | 6/1991 | Salort | |
| 5,163,450 A | 11/1992 | Cadichon et al. | |
| 5,188,587 A | 2/1993 | McGuire et al. | |
| 5,203,763 A | 4/1993 | Lajiness-O'Neill | |
| 5,410,756 A | 5/1995 | Hutson | |
| 5,489,259 A * | 2/1996 | Jacobs et al. | 602/13 |
| 5,628,725 A | 5/1997 | Ostergard | |
| 6,106,493 A | 8/2000 | Rozell | |
| 6,322,528 B1 | 11/2001 | Kania | |

OTHER PUBLICATIONS

International Application No. PCT/US/01/05300, PCT Written Opinion under Rule 66 (mailed Jan. 29, 2002).
International Application No. PCT/US/01/05300, PCT International Search Report under Rule 44.1 (mailed Jun. 26, 2001).
International Application No. PCT/US99/16694, PCT Written Opinion under Rule 66 (mailed Nov. 15, 2000.
International Application No. PCT/US99/16694, PCT International Search Report under Rule 44,1 (mailed Nov. 17, 1999).

* cited by examiner

*Primary Examiner*—Henry Bennett
*Assistant Examiner*—Shumaya B. Ali

(57) ABSTRACT

A shoulder brace (10) including front (80) and rear pressure pads to be respectively positioned on front and rear portions of an individual's shoulder joint, a support member (18) to be positioned at a mid-section of the individual, a front frame member connected to the support member and the front pressure pad, and a rear frame member connected to the support member and the rear pressure pad. Also included is an arm cuff to be positioned on the arm of the individual, and a compression mechanism (20) configured to compress the front and rear frame members in accordance with a movement of the individual's arm such that the front and rear pressure pads press against the individual's shoulder joint.

14 Claims, 27 Drawing Sheets

SHOULDER BRACE

CROSS-REFERENCE TO A RELATED APPLICATIONS

This application is related to U.S. Patent Application Ser. No. 09/363,924, filed on Jul. 30, 1999; U.S. Patent Application Ser. No. 09/506,012, filed on Feb. 17, 2000; U.S. Patent Application Ser. No. 60/183,559, filed on Feb. 18, 2000; and Internation Patent Application No. PCT/US 01/05300, filed on Feb. 20, 2001, all of which are incorporated herein in their entirety.

BACKGROUND OF THE INVENTION

1. Field of the Invention

The present invention relates generally to orthopedic braces, particularly to a shoulder brace for providing support to the shoulder area.

2. Description of the Related Art

The ball and socket joint of the human shoulder provides for free movement of the arm. The area of contact between the various bones in the shoulder is minimal and the shoulder joint is dependent upon surrounding muscles, and to a lesser extent ligaments, tendons and fibrocartiledge, for its integrity and functionality. The muscular and bone composition of the shoulder is the subject of extensive medical study and while a more detailed discussion of the anatomy of the shoulder is not necessary for the purposes here, such a discussion can be found in most basic human anatomy books. Because of its construction, the shoulder joint is capable of flexion, extension, abduction, adduction, rotation and circumduction movement. Also because of its construction, the shoulder joint is susceptible to a great number of injuries.

Injuries are commonplace in various activities that require constant motion of the shoulder joint or subject the shoulder to stress. For example, the overhand throwing motion used in baseball is an unnatural motion that can cause shoulder muscle strains or tears, including injury to the deep rotator muscles or rotator cuff of the shoulder and arm. Participants in contact sports such as rugby and football often suffer shoulder injuries, e.g., dislocation of the ball and socket joint as well. Once an injury to the shoulder area has occurred, it is frequently necessary to support the joint area to both facilitate the convalescing process in certain situations, and minimize discomfort due to the injury. Additionally, it is advantageous to provide support to the shoulder area to help prevent shoulder injuries to individuals who are particularly susceptible to such injuries.

Anterior shoulder instability most commonly develops when the restraints of the humeral head are inadequate or excessive force is being applied, usually when the shoulder is in abduction, external rotation, and extension. Anterior shoulder stability is usually maintained by the anteroinferior glenohumeral ligament as well as the subscapularis muscle and the middle glenohumeral ligament. Weakness in these allows excessive anterior translation of the humeral head in the glenoid fossa, the humeral head being the ball and the glenoid fossa being the socket of what is commonly referred to as the ball and socket joint of the shoulder. Since the anteroinferior glenohumeral ligament is especially stressed when the arm is positioned in abduction, extension or external rotation, it is reasonable to assume that preventing or limiting these positions might be beneficial for patients with instability. However, by preventing or limiting those positions, athletes who suffer these types of injuries or weaknesses would be particularly impaired in their ability to perform their respective activity.

There are a number of braces and harnesses known in the art that alleviate pressure on various points of the shoulder joint. For example, U.S. Pat. No. 3,906,944 issued to Christian discloses a shoulder harness that prevents damage to the muscles, tendons and ligaments in the shoulder area and also provides support to prevent the dislocation of the shoulder. The shoulder harness disclosed in the Christian patent, however, severely restricts the movement of the upper arm with respect to the shoulder, thereby restricting the movement of the ball and socket joint. Furthermore, existing braces, such as the Christian harness, are cumbersome and difficult for a wearer to put on, particularly because of the shoulder injury. Most known braces and harnesses also neither allow the wearer to increase or decrease the amount of support around the area of the shoulder, nor are capable of being adjusted to conform to the particular body size of the wearer.

Furthermore, known shoulder braces are generally excessively restrictive on arm movement while they provide inadequate support for preventing anterior dislocation of the shoulder joint.

U.S. Pat. No. 5,188,587 issued to McGuire et al. teaches an active shoulder brace made of a resilient fabric-like material. The shoulder brace taught by McGuire et al. includes a sleeve portion which is designed to fit around the upper end of the upper arm of a patient and it includes straps that are wrapped over and around the sleeve portion and attached to a torso belt which anchors the straps attached to the sleeve portion. When a patient wearing the shoulder strap taught by McGuire et al. raises their arm, the straps tighten and provide support to the shoulder joint.

However, as with the other known shoulder straps, the shoulder strap taught by McGuire et al. exerts a substantial amount of force to the top of the shoulder and the upper arm when the patient wearing the strap raises their arm and far less pressure or support to the anterior, posterior and medial side of the shoulder joint. The result is that the shoulder strap provides a strong force which inhibits upward movement of the arm of the patient yet provides only moderate or little support or pressure to the anterior, posterior and medial sides of the shoulder joint. As discussed above, patients with chronically dislocating shoulders experience problems with the humeral head of the shoulder moving in an anterior direction out of the glenoid fossa and thereby dislocating. Therefore, the shoulder straps of the prior art provide an excessive amount of force that inhibits motion of the arm while ineffectively preventing the anterior dislocation of the shoulder joint. Therefore, it is desirable to provide a shoulder brace which can compensate for weaknesses in tissues such as the glenohumeral ligament, the subscapularis muscle and the middle glenohumeral ligament, without causing excessive restriction to arm movement.

SUMMARY OF THE INVENTION

It is therefore desirable and an object of the present invention to provide a shoulder brace that provides strong posterior, anterior and/or medial pressure to the shoulder joint of a patient wearing the shoulder strap while not excessively inhibiting motion of the arm. Movement of a patient's shoulder can be broken down into safe zones and danger zones. When a patient moves their arm so that their elbow is above the shoulder joint when the patient is in a standing position, or when the elbow is behind the plane passing between the front and rear side of the body, or when the arm is in excessive external rotation, movements into any such areas would be into a danger zone where the likelihood of an anterior dislocation greatly increases. Furthermore, if such a movement occurs during an athletic activity, where other forces and stresses are exerted upon the shoulder joint, the chances of an anterior dislocation are even greater.

It is a further object of the present invention to provide a shoulder brace that provides anterior and posterior compression of the shoulder joint when the arm of the patient is moved into a danger zone.

It is a further object of the present invention to provide a shoulder brace that is less intrusive than that of the braces used in the prior art, causing less interference with a patient's movements and allowing greater range of motion.

It is yet another object of the present invention to provide a shoulder brace that can provide anterior and posterior compression of a shoulder joint without inhibiting motion of the patient's arm in the upward direction.

These and other objects are achieved according to the present invention by providing a shoulder brace including a shoulder member mountable to a shoulder of a patient's arm, and a positioning device configured to increase a pressure to the shoulder of the patient in accordance with a position of the user's arm.

In one embodiment of the present invention, the shoulder brace includes a shoulder member mountable to a shoulder of a patient's arm with an open portion forming substantially rigid first and second arms and a positioning device configured to vary the spacing of the first and second arms according to the position of the patient's arm. By constructing the shoulder brace as such, the present invention avoids undue restriction of movement of the user's arm while efficiently transforming the energy directed into the shoulder brace by the movement of the user's arm into a pressure to the user's shoulder.

According to another embodiment of the present invention, the positioning device includes a tensioning ring and first and second tension triggering straps configured to provide anterior and posterior compression of the shoulder joint when the arm of the patient is moved into a danger zone.

According to another embodiment of the present invention, the shoulder brace includes a first mounting member mountable to a user's pectoral area, a second mounting member mountable to a user's upper arm, and a connecting member connected to the first mounting member at a first end, and connected to the second mounting member at a second end. Additionally, a positioning device is configured to increase a pressure to the user's shoulder according to the movement of the user's arm. By constructing the shoulder brace as such, the shoulder brace efficiently communicates movements of the user's upper arm to the shoulder brace to thereby effect the pressure directed to the shoulder joint.

BRIEF DESCRIPTION OF THE DRAWINGS

FIGS. 37–41 are copies of photographs of a person wearing the shoulder brace shown in FIGS. 30, 31 and 32.

DESCRIPTION OF THE PREFERRED EMBODIMENTS

Figure 1:
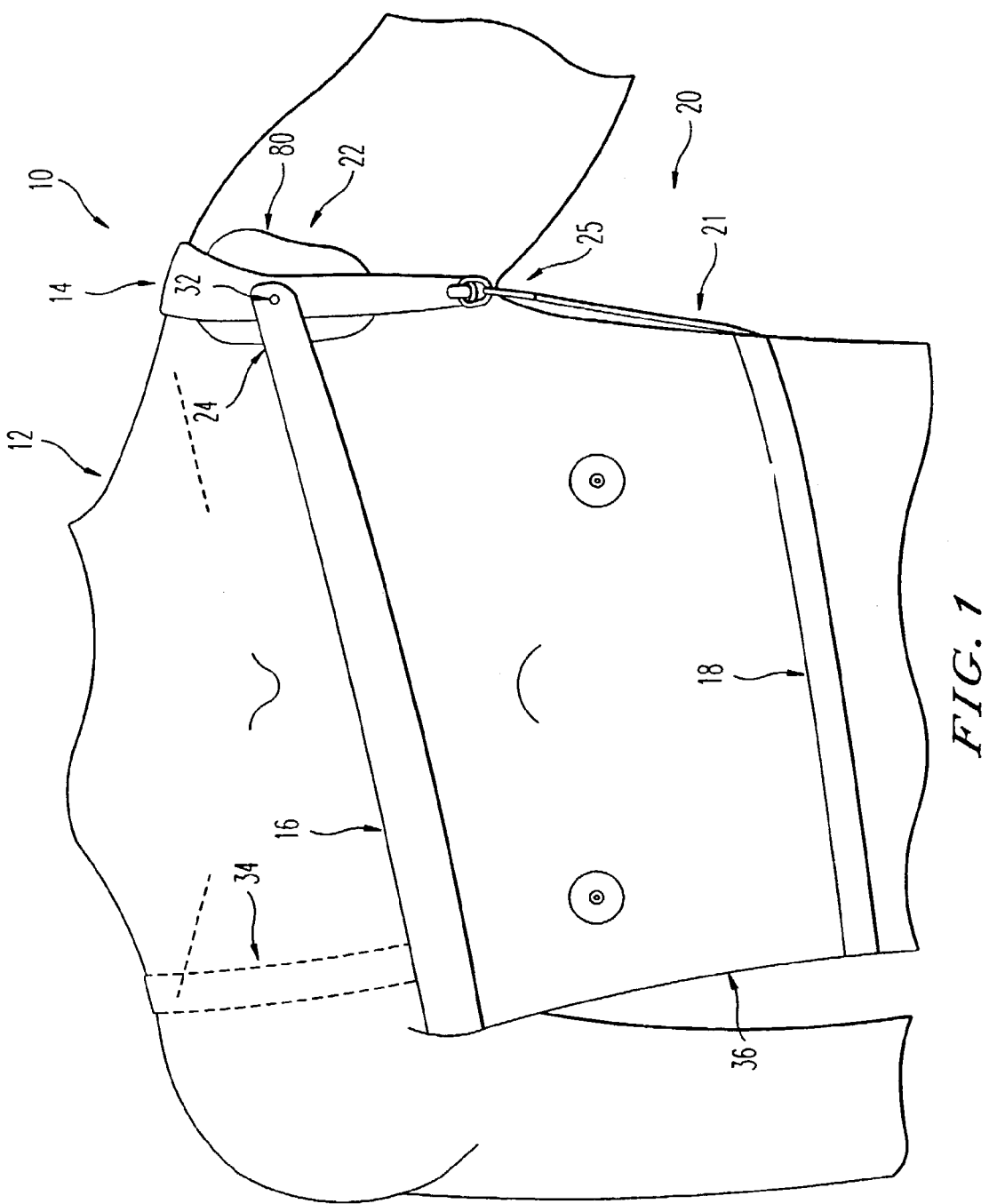
FIG. 1 is a front view of a patient wearing a shoulder brace according to the present invention.
Figure 2:
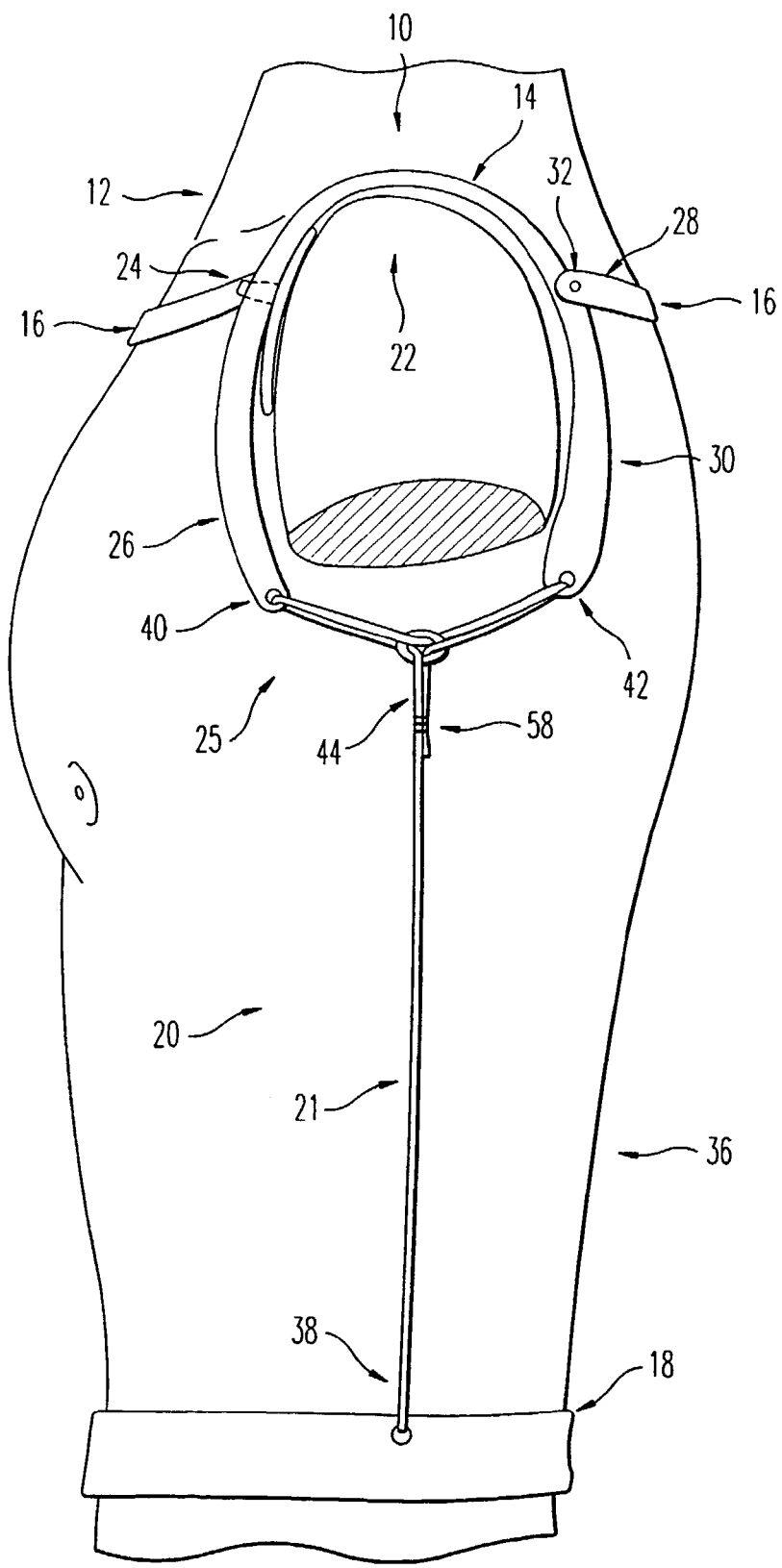
FIG. 2 is a side view of the shoulder brace shown in FIG. 1.

Referring now to the nonlimiting example of the drawings, wherein like reference numerals designate identical or corresponding parts throughout the several views, and more particularly to FIGS. 1 through 4, thereof, a shoulder strap 10 being worn by a patient 12 is generally shown. Shoulder brace 10 generally includes shoulder joint member 14, and positioning device 20. As shown in FIGS. 1 and 2, shoulder joint member 14 is generally annularly shaped so as to fit generally over a shoulder joint 22 of a patient 12. Brace 10 may optionally include alignment strap 16 which generally has a front end 24 attached to a front arm 26 of shoulder joint member 14 and a rear end 28 attached to a rear arm 30 of shoulder joint member 14. Preferably, front end 24 and rear end 28 of alignment strap 16 are attached to shoulder joint member 14 at a pivot 32. Such a pivot allows the shoulder joint member 14 to rotate relative to anchor strap 16 when a patient raises their arm, without significant impingement or distortion of the strap 16 or shoulder joint member 14. Additionally, strap 16 may be made of elastic, or include an elastic portion (not shown) so as to provide a bias pulling shoulder joint member 14 towards the torso of the patient.

Figure 3:
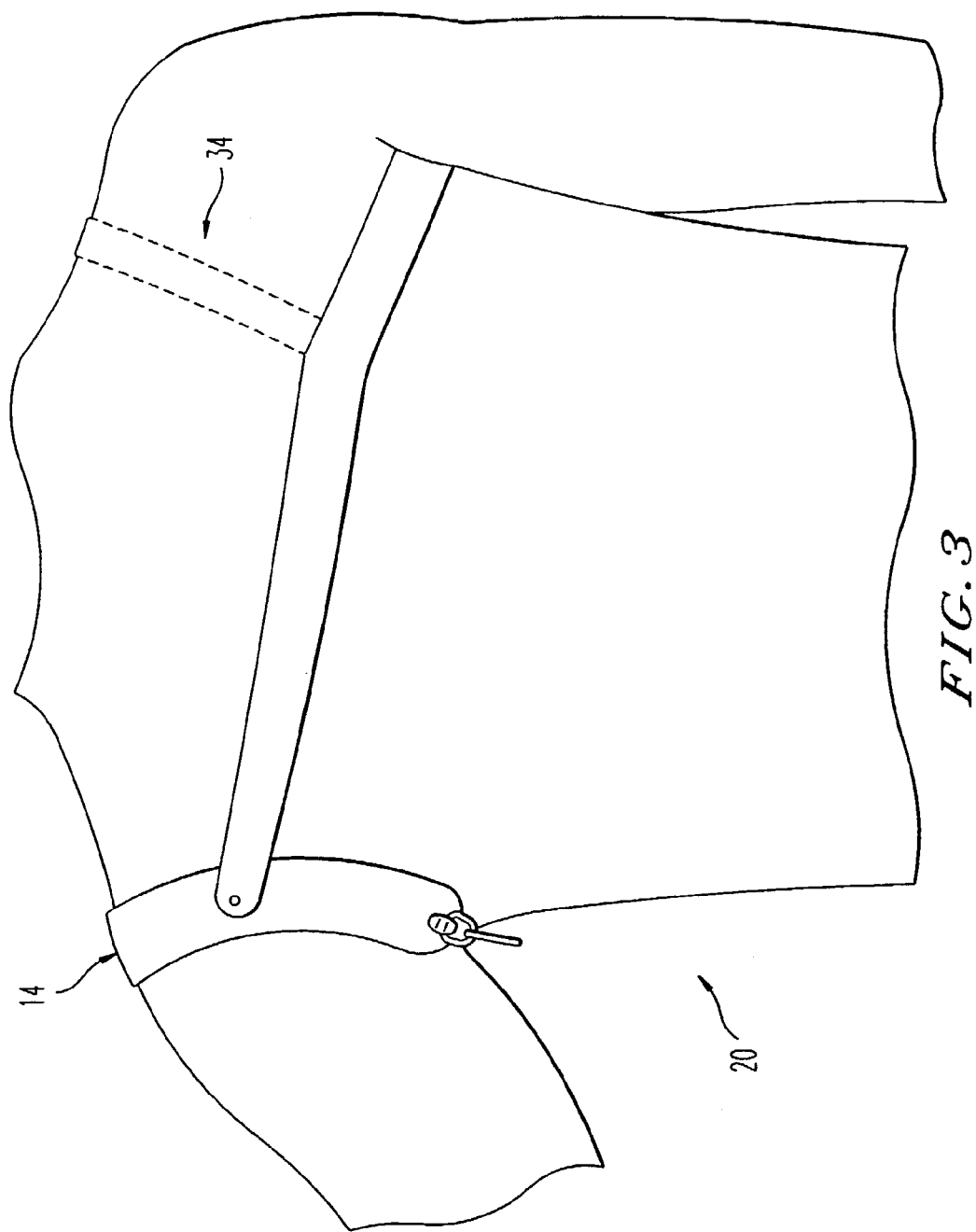
FIG. 3 is a rear view of the shoulder brace shown in FIG. 1.

Alignment strap 16 may also include a support strap 34 shown in phantom lines in FIGS. 1 and 3, thereby ensuring that alignment strap 16 does not inadvertently fall from a proper alignment for maintaining shoulder joint member 14 in alignment with a patient's shoulder joint 22.

As shown in FIGS. 1 and 2, anchor strap 18 is wrapped around a patient's torso 36. Anchor strap 18 is preferably positioned according to the preferences of the patient. As shown in FIG. 1, anchor strap 18 is provided in an upper abdominal region of the patient's torso 36. However, as shown in FIG. 2, anchor strap 18 may alternatively be provided approximately around the patient's waste. Additionally, anchor strap 18 may be provided in other configurations discussed in greater detail later.

Figure 4:
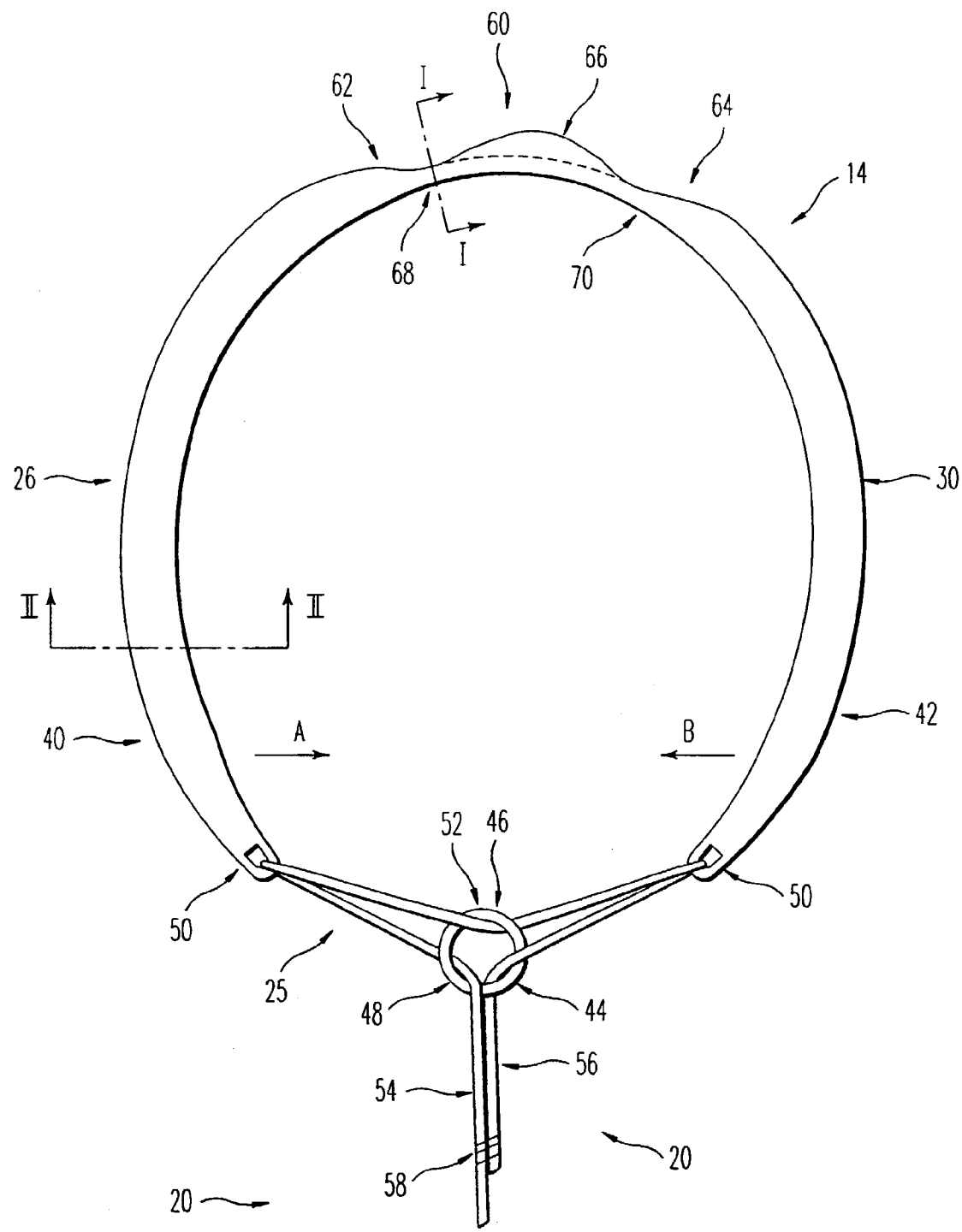
FIG. 4 is an enlarged view of the shoulder brace shown in FIG. 1.
Figure 5:
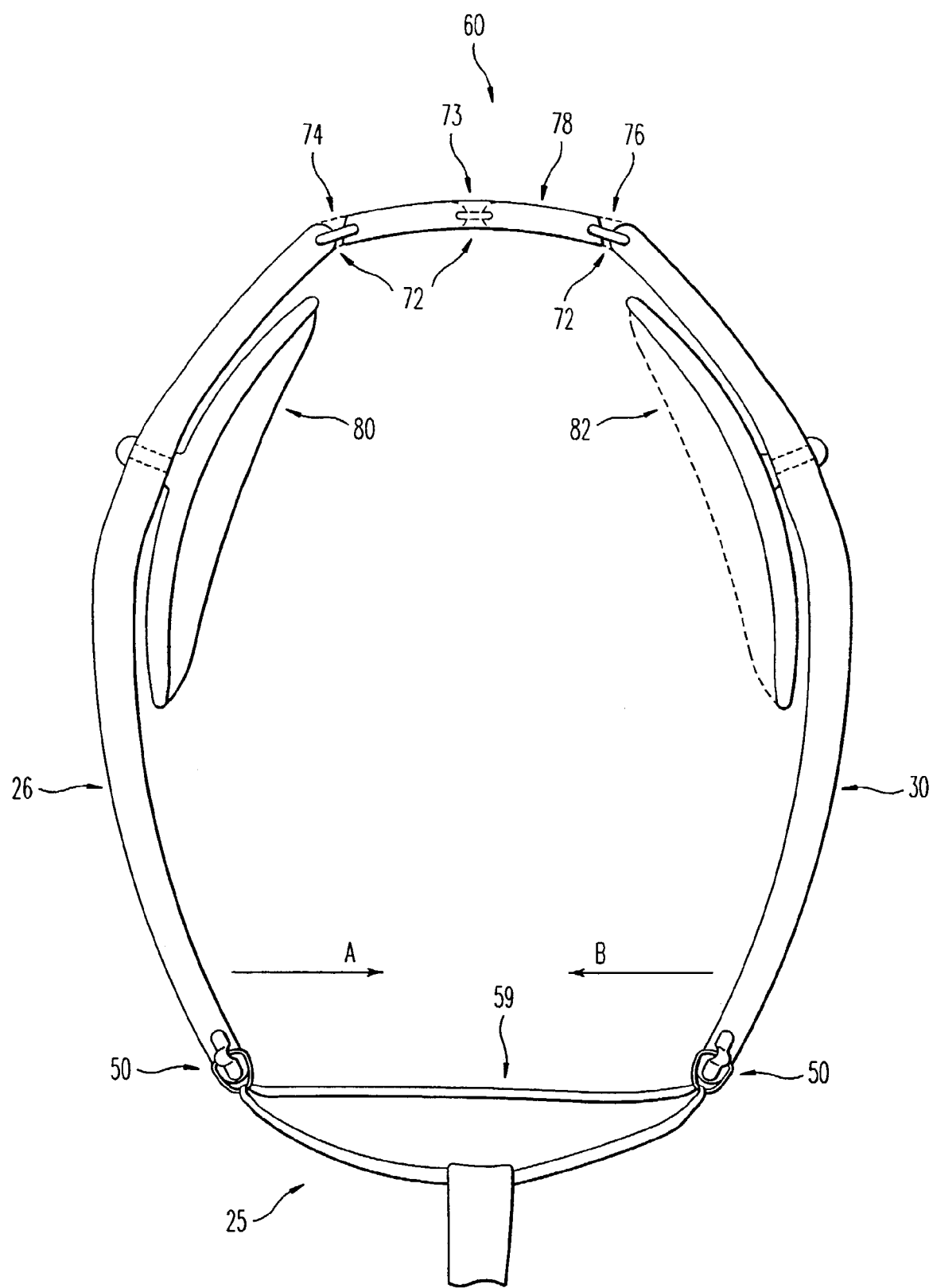
FIG. 5 is a side view of an alternative embodiment of the shoulder brace according to the present invention.

Positioning device 20 may be comprised of tension triggering strap 21 and a positioning unit 25. In this embodiment, triggering strap 21 is connected at lower end 38 to anchor strap 18 and connected to front lower end 40 and rear lower end 42 of shoulder joint member 14 at an upper end 44 of strap 21. Tension triggering strap may be constructed out of any flexible material formed into any shape including a woven cable or a band. In this embodiment, positioning unit 25 is constructed of tensioning ring 46 and eyelets 50 which are constructed to receive one end of triggering strap 21. As better seen in FIG. 4, strap 21 is first threaded through tensioning ring 46 at a lower end 48 of tensioning ring 46, then through eyelets 50 formed on lower ends 40 and 42 of shoulder joint member 14 and then through an upper end 52 of tensioning ring 46. More specifically, a first portion 54 of strap 21 is threaded upwards through tensioner ring 46 then through eyelet 50 of front lower portion 40 of shoulder joint member 14 through the upper portion 52 of tensioning ring 46, then through eyelet 50 of rear lower portion 42 of shoulder joint member 14 then again through lower portion 48 of tension ring 46 wherein a double-back portion 56 of strap 21 is secured to the first portion 54 of strap 21 with a binder 58. Threaded as such, strap 21 is guided through tensioner ring 46 such that when strap 21 is provided with tension when a patient wearing the shoulder brace 10 raises their arm, the positioning device 20 contracts shoulder joint member 14 such that front arm 26 of shoulder joint member 14 is compressed towards rear arm 30 so as to cause an anterior-posterior compression of the shoulder joint. By threading strap 21 through tensioner ring 46 as such, positioning device 20 efficiently transmits the downward pulling of strap 21 through the ring to the eyelets 50 of shoulder joint member 14 in a direction nearly perpendicular to the direction strap 21 enters tensioning ring 46. Thereby, positioning device 20 transmits nearly a 1:1 ratio of compression between eyelets 50 to the length of strap 21 pulled downward through tensioner ring 46. Furthermore, tensioner ring 46 is maintained in the vertical position shown by the tension in strap 21 since strap 21 is threaded through tensioner ring 46 and contacts it at the upper portion 52 of tensioner ring 46, as shown in FIG. 4. However, positioning device 20 may take other forms, such as that shown in FIG. 5, where tension triggering strap 23 is made from a wide strap such as a nylon strap and where positioning unit 25 includes tensioning loop 59 and eyelets 50 wherein triggering strap 23 is connected to loop 59. Also shown in FIG. 5 is an alternative design for eyelets 50 formed on the front and rear lower ends of shoulder joint member 14. As shown there, eyelets 50 are constructed of metal rings connected to ends 40 and 42.

Referring again to FIGS. 1 through 4, shoulder joint member 14 is preferably generally annularly shaped with a front arm 26 and a rear arm 30. In order to provide efficient transfer of the pulling force generated in positioning device 20 by the upward movement of a patient's arm into a compression force, preferably an anterior-posterior compression of the shoulder joint by the movement of front arm 26 and rear arm 30 towards each other in the direction of arrows A and B respectively, shoulder joint member 14 includes a flexible portion 60 formed between arms 26 and 30. By providing a flexible portion 60 between arms 26 and 30, shoulder joint member 14 is more easily compressed in the directions of A and B as compared to an annular member with uniform rigidity. Also preferably, front arm 26 and rear arm 30 are constructed so as to be substantially rigid. Constructed as such, the relatively rigid arms 26 and 30 efficiently transfer the compression force in the directions of A and B while flexible portion 60 allows arms 26 and 30 to move in directions A and B without excessive resistance.

By aligning arms 26 and 30 as such, arms 26 and 30 will apply a direct force in directions of A and B and thereby stabilize the glenohumeral head. It is also conceived, however, that arms 26 and 30, or other members (not shown) could be arranged at other locations on the arm so that a force is can be applied on the arm and close enough to the shoulder joint so that the resultant indirect force would provide sufficient posteriorward force on the humeral head, in an indirect manner.

Shoulder joint member 14 can be constructed from a single piece as shown in FIG. 4. When constructed as such, the rigidity of joint member 14 can be varied along its length by changing its cross-sectional shape. For example, as shown in FIG. 4, the cross-sectional thickness of Joint member 14 can be made relatively thick along front and rear arm portions 26 and 30 and relatively thinner at flexible portions 60 between decreasing thickness sections 62 and 64. Flexible portion 60 may have a uniform thickness across its length such as that shown in the broken line in FIG. 4. Alternatively, flexible portion 60 may have a spacing portion 66 which is relatively thicker than flexible portion 60. By providing flexible portion 60 with a spacing portion 66, flexible portion 60 is effectively broken into two flexible portions, front flexible portion 68 and rear flexible portion 70. By constructing the flexible portion 60 as such, impingement of the upper portion of a patient's shoulder can be reduced since the folding or creasing of shoulder joint member 14 is inhibited when front arm 26 and rear arm 30 are moved towards each other in directions A and B, respectively.

Referring now to FIG. 5, flexible portion 60 may optionally be constructed with hinges 72. In the embodiment shown in FIG. 5, flexible member 60 may be constructed with a single hinge 73 or the combination of a front hinge 74, a rear hinge 76 and a spacer element 78. Similar to the function of the front and rear flexible portions 68 and 70 shown in FIG. 4, front and rear hinges 74 and 76 similarly can reduce impingement of the upper part of the patient's shoulder when the front and rear arms 26 and 30 of shoulder joint member 14 are moved towards each other in the direction of arrows A and B, respectively.

Figure 4A:
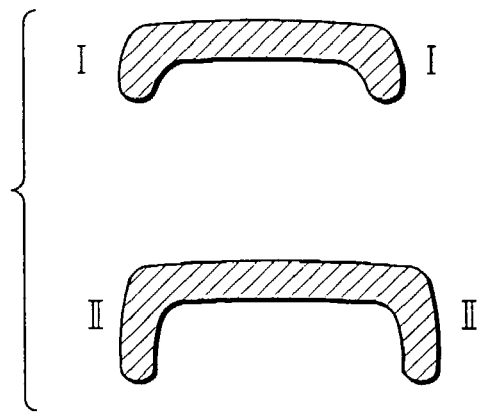
FIGS. 4a, 4b and 4c are cross-sectional views I—I and II—II shown in FIG. 4.
Figure 4B:
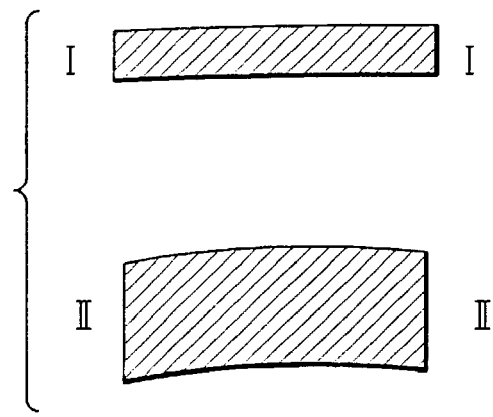
Figure 4C:
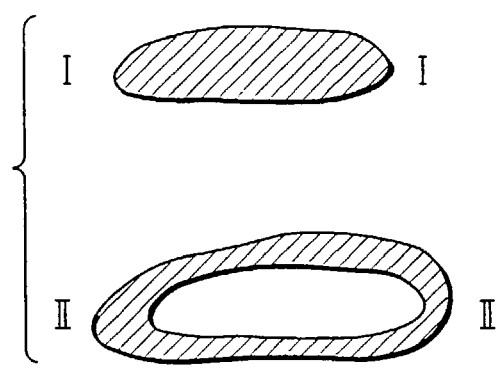

As discussed above, in order to produce areas of differing rigidity, shoulder joint member 14 may be provided with cross-sections of varying shape or size along its length. Referring now to FIGS. 4a, 4b and 4c, optional cross-sectional shapes are shown for the cross-sections at I—I for front flexible portion 68 for example and cross-section II—II for the rigid portion of front arm 26. As shown in FIG. 4a, cross-sections I—I and II—II can be of a channel shape wherein the cross-section at I—I is more shallow relative to the depth of the cross-section at II—II. FIG. 4b shows a cross-sectional that is a solid rectangle. FIG. 4c shows a cross-section that is oval wherein the cross-section at II—II is substantially hollow thereby providing for a lightweight design which does not have sharp edges on an outer surface so as to cause unattractive protrusions in the outer clothing of a patient wearing the shoulder strap. By providing for the reduced thickness cross-section at flexible portions 68 and 70, those portions are more flexible and thereby provide the flexation which allows shoulder joint member 14 to compress in the directions of A and B without excessive resistance. Furthermore, by providing front arm 26 and rear arm 30 with increased cross-sectional depth such as those shown in FIGS. 4a through 4c, arms 26 and 30 efficiently transfer the compression force imparted upon arms 26 and 30 by positioning device 20 to the anterior and posterior areas of a patient's shoulder joint 22, similar to the operation of a hand-held nut-cracker. Although the cross-sections shown in FIGS. 4a through 4c are not drawn to scale, they are meant only to illustrate the concept of reducing the width or thickness of the cross-section of the joint shoulder member 14 to provide for relatively rigid portions and relatively flexible portions. Using such a configuration, the shoulder joint member 14 can be made out a variety of materials including thermoplastics and other composite materials such as carbon fiber. Although, when using more brittle or fatigue sensitive materials such as carbon fiber or metals such as aluminum or titanium, it may be necessary to use hinges rather than areas of reduced cross-sectional thickness in order to allow the shoulder joint member to compress in the directions of arrows A and B without excessive resistance.

In order to provide greater comfort to a patient wearing the shoulder strap according to the present invention, the shoulder strap preferably includes cushion 80 which is positioned to be aligned generally with the anterior portion of a patient's shoulder joint 22. Preferably, cushion 80 is shaped to evenly distribute the compression forces transmitted to it by the compression of front arm 26 towards rear arm 30 yet small enough so as to minimize impingement of the pad when the patient moves their arm towards their chest, i.e., adduction. Shoulder joint member 14 may also be provided with a rear cushion 82 so as to provide additional comfort for the patient's back upon compression of front arm 26 and rear arm 30 towards each other in the directions of arrows A and B, respectively. Cushions 80 and 82 may be constructed of any known cushioning material such as foam, rubber compounds, or other soft materials, but are preferably constructed of PDE.

Figure 6:
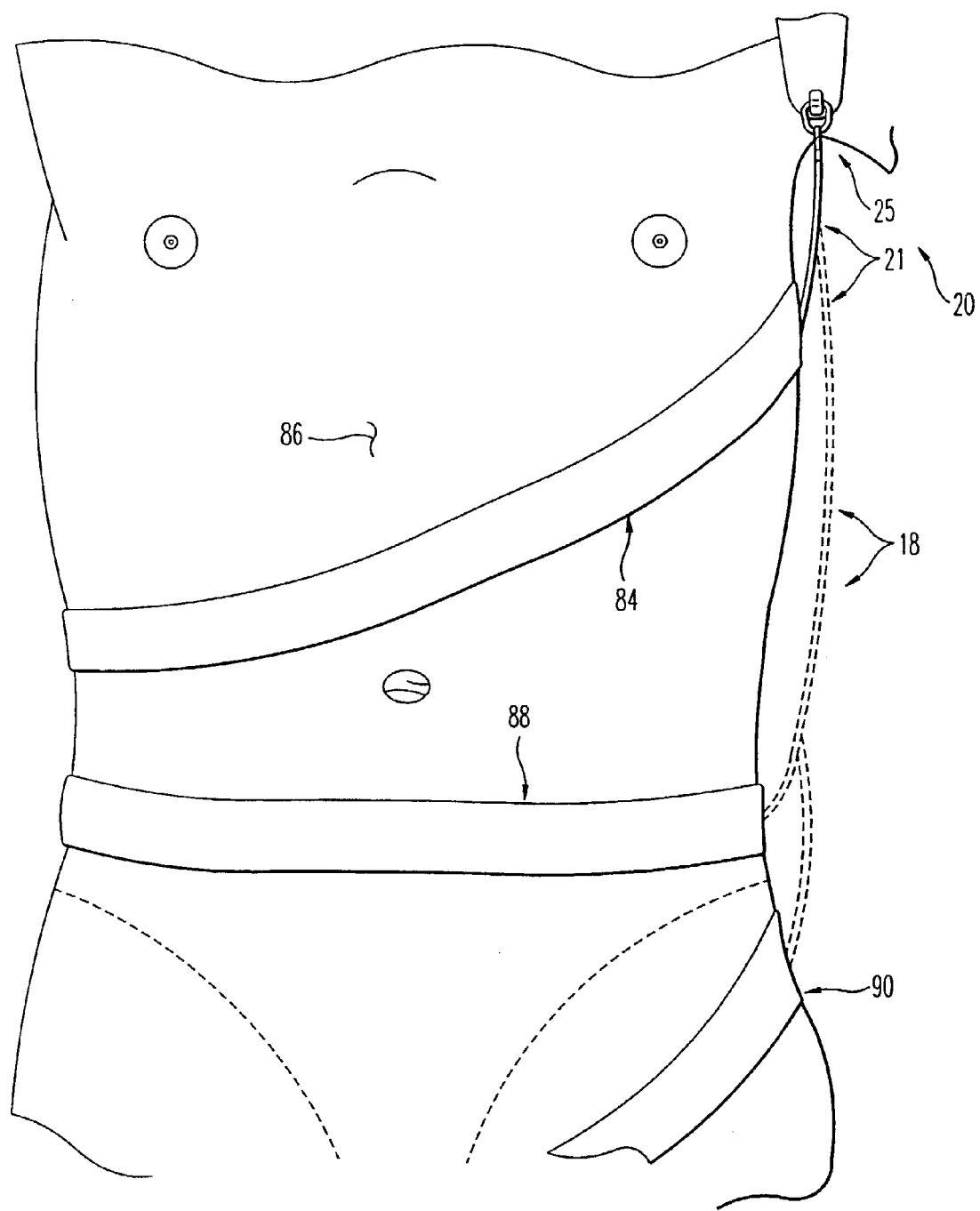
FIG. 6 is a front view of an anchor strap according to the shoulder brace of the present invention.
Figure 7:
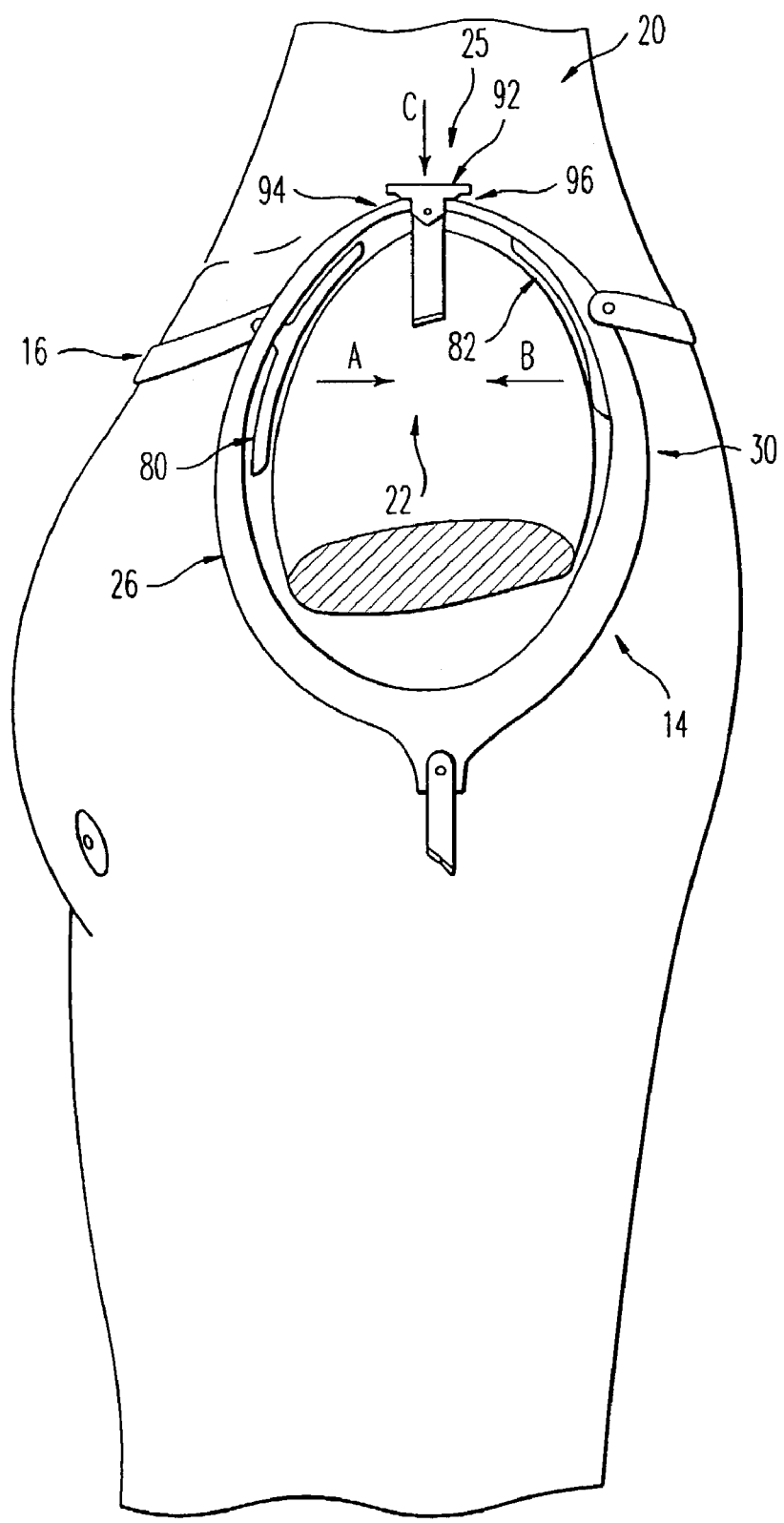
FIGS. 7 and 8 are side views of a further embodiment of the shoulder brace of the present invention.

Referring now to FIG. 6, an alternative embodiment of anchor strap 18 is shown. As shown in the figure, anchor strap 18 may be constructed as strap 84 such that it wraps diagonally around an upper abdominal region of 86 of a patient. Alternatively, the anchor strap may be constructed as strap 88 which wraps around a patient's waste or hips or finally, anchor strap 18 may be wrapped around a patient's upper thigh as strap 90. In each case, tension triggering straps 21 or 23 would be attached to the anchor strap in an area below the patient's arm as shown in the solid and dotted lines. However, it has been found that straps such as 88 and 90 are less stable, less comfortable and/or are affected by other body motions, and are thereby less reliable in providing tension to shoulder strap member 14 to compress front and rear arms 26 and 30. Therefore, strap 84 is the preferred configuration of anchor strap 18.

Figure 8:
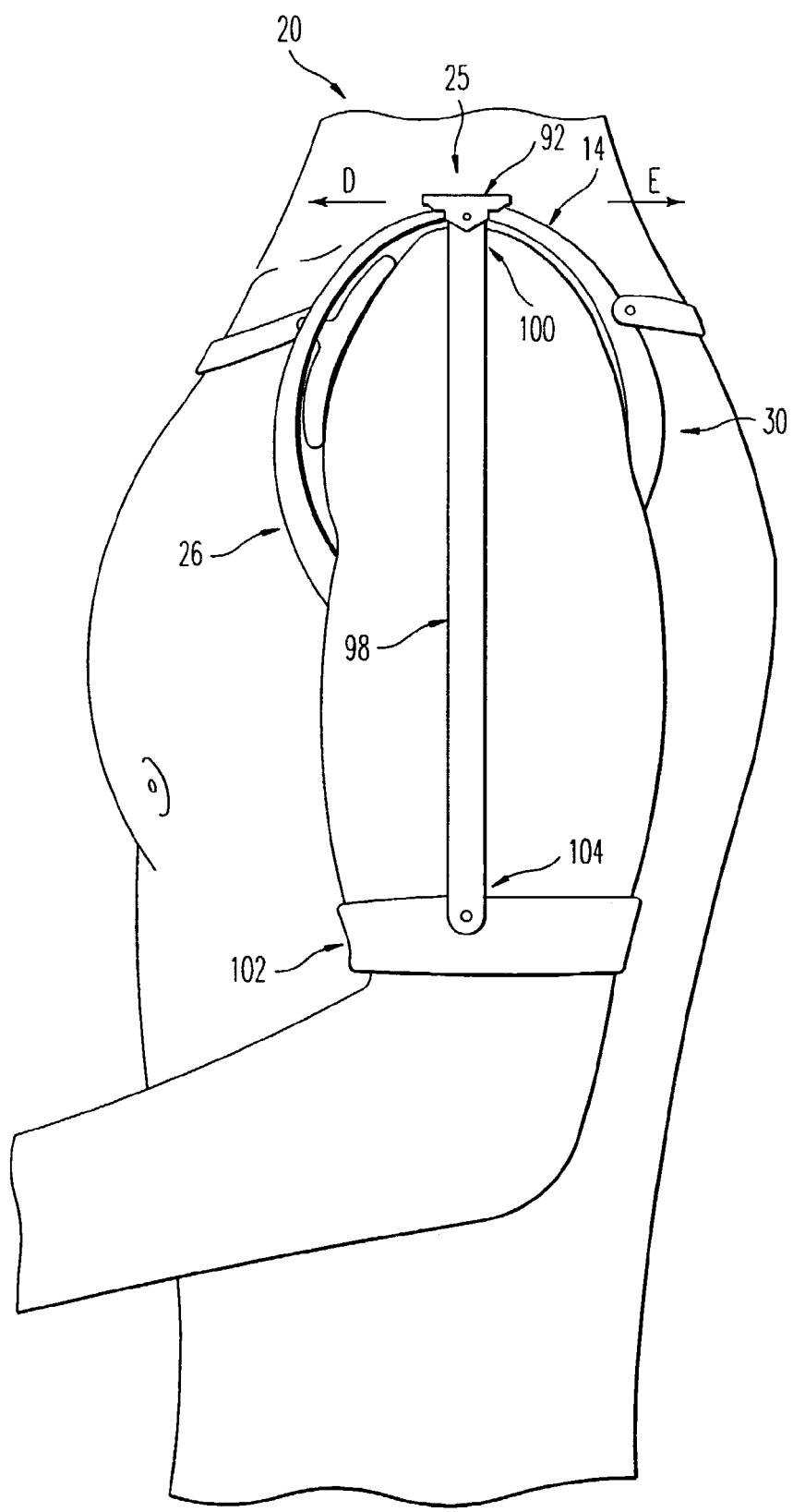
Figure 9:
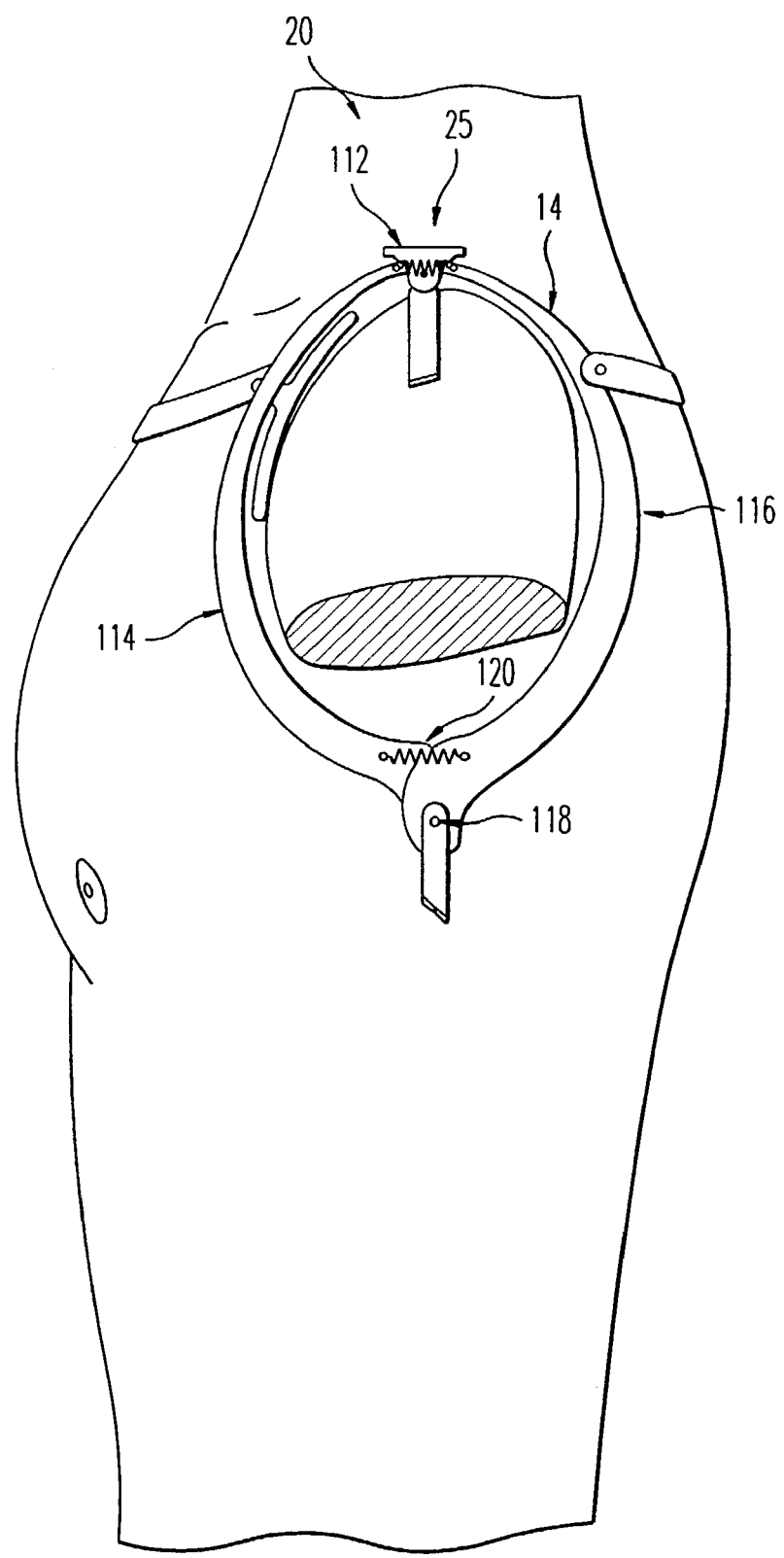
FIG. 9 is a further embodiment of the shoulder brace according to the present invention.

Referring now to FIGS. 7–15, a further embodiment of the present invention is shown therein. As shown in the figures, positioning unit 25 includes a relaxing device 92 connected between the two open ends 94 and 96 of shoulder joint member 14. As in the previous embodiment, shoulder joint member 14 can be held in place by alignment strap 16, around the shoulder joint of a patient. Optionally, the shoulder brace in this embodiment can include a cushion 80 alone or in addition to a rear cushion 82. In this embodiment, shoulder joint member 14 is biased in a direction so as to compress in an anterior-posterior direction shoulder joint 22 of a patient, so that the front arm 26 and rear arm 30 of shoulder joint member 14 are biased in the directions of arrows A and B respectively. Relaxing device 92 is configured such that when it is urged downward in the direction of arrow C, the open ends 94 and 96 of shoulder joint member 14 are spread apart thereby relaxing the compression in the direction of arrows A and B on the shoulder joint 22. In order to urge relaxing device 92 in the downward direction, tension triggering strap 98 is connected to relaxing device 92 at upper end 100 and attached to anchor strap 102 at lower end 104, as shown in FIG. 8. Connected as such, when a patient has their arm in a lowered position, such as that shown in FIG. 8, tension triggering strap 98 is pulled in a downward direction as viewed in FIG. 8 thereby pulling relaxing device 92 in a downward direction and thereby spreading front arm 26 and rear arm 30 of shoulder joint member 14 in the direction of arrows D and E, respectively.

Figure 10:
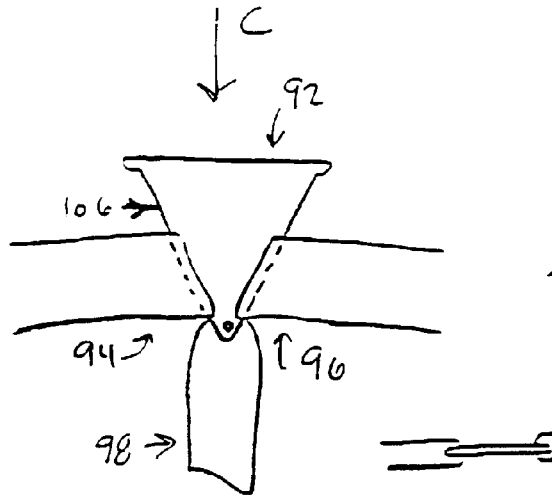
FIGS. 10–15 are side views of further embodiments of biasing and relaxing devices according to the present invention.
Figure 11:
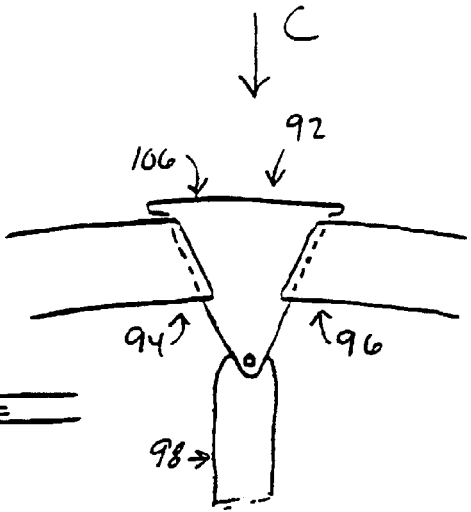
Figure 12:
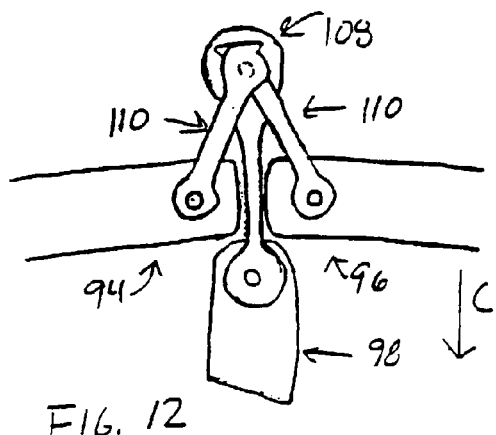

As better seen in FIGS. 10 and 11, relaxing device 92 comprises a wedge-shaped member 106 that is configured to be received by the open ends 94 and 96 of shoulder joint member 14 such that as wedge-shaped member 106 is pulled downward in the direction of arrow C, to the downward position shown in FIG. 11, open ends 94 and 96 of shoulder joint member 14 are pushed apart thereby relaxing the anterior-posterior contraction of the shoulder joint member 14.

By constructing shoulder joint member 4 so that it biased in a compressive state, and providing a relaxing device for opposing the bias of the shoulder joint member 14, the shoulder brace according to this embodiment operates in a substantially opposite manner as that of the previous embodiment. For example, in the previous embodiment, the energy transferred to the shoulder joint member 14 by the movement of the patient's arm in an upward direction caused the shoulder joint member 14 to be compressed in an anterior-posterior direction which thereby inherently causes at least some resistance to the patient's arm movement. However, in the present embodiment, shoulder joint member 14 is biased toward a compressive state, and is released when the patient moves their arm in an upward direction. Furthermore, because relaxing device 92 maintains tension in tension triggering strap 98 when the patient's arm is in a lowered position, the tension in tension triggering strap 98 aids the patient in raising their arm, while gravity aids in lowering of the arm. This embodiment thereby provides a substantial benefit to patients suffering from a serious injury or disability where any resistance to the movement of their arm in an upward direction would prevent them from moving their arm at all, which thereby enhances the disability, and slows physical therapy and recovery.

Figure 13:
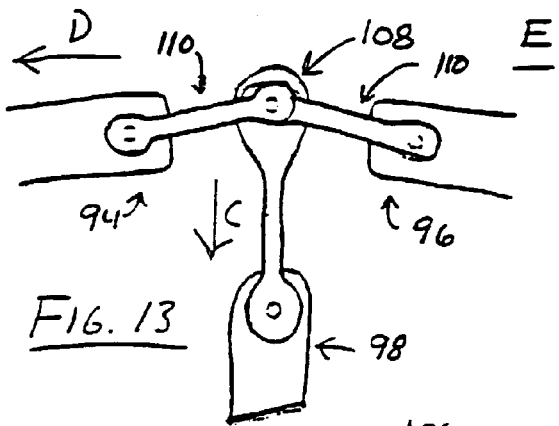
Figure 14:
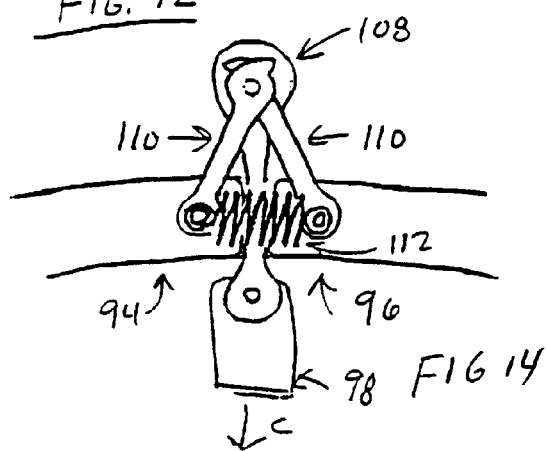
Figure 15:
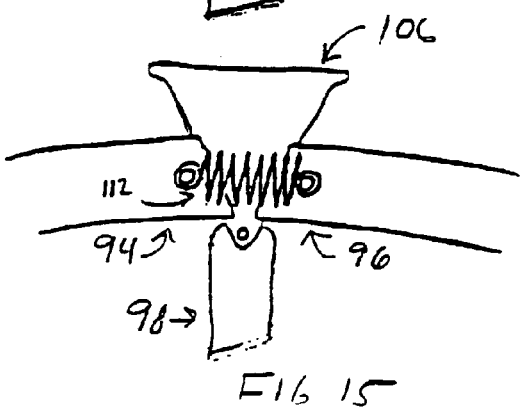

As shown in FIGS. 12–15, the relaxing device can be constructed in a number of ways. For example, the relaxing device 92 shown in FIGS. 12–14, includes a pivot boss 108 which is oriented vertically between the free ends of shoulder joint member 14, as viewed in FIGS. 12–14, and a pair of pivot rods 110. Similar to the operation of the wedge-shaped member 106, when the tension triggering strap 98 is pulled in a direction of arrow C, pivot rods 110 are urged to rotate in the direction of arrow C, and therefor push the open ends 94, 96 of shoulder joint member 14 apart in the direction of arrows D and E, respectively, as shown in FIG. 13. Although this embodiment requires a greater number of moving parts, this embodiment inherently has less frictional resistance compared to the operation of the wedge-shaped member 106. FIGS. 14 and 15 show further embodiments of the relaxing device 92 where an upper biasing device 112 such as a spring. In this embodiment, shoulder joint member 14 may be constructed of two separate pieces 114 and 116 which are attached at hinge 118. In order to provide a bias to joint member 14, when it is constructed as such, a lower biasing member 120 such as a spring may be used and optionally an additional upper biasing member may be used. This arrangement would be particularly useful when shoulder joint member 14 is constructed of brittle and/or fatigue sensitive materials such as resin-matrix composites such as carbon fiber, or metals such as aluminum or titanium.

Figure 16:
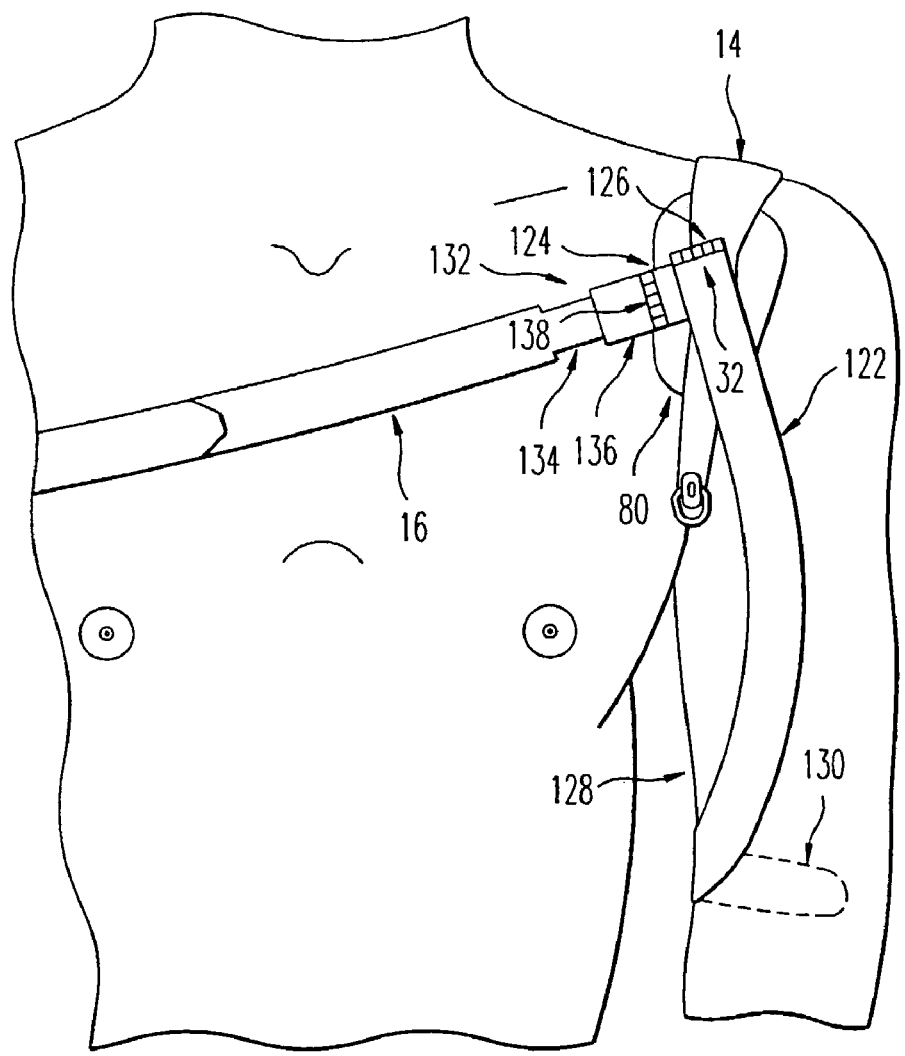
FIG. 16 is a further embodiment of the shoulder brace of the present invention.
Figure 20:
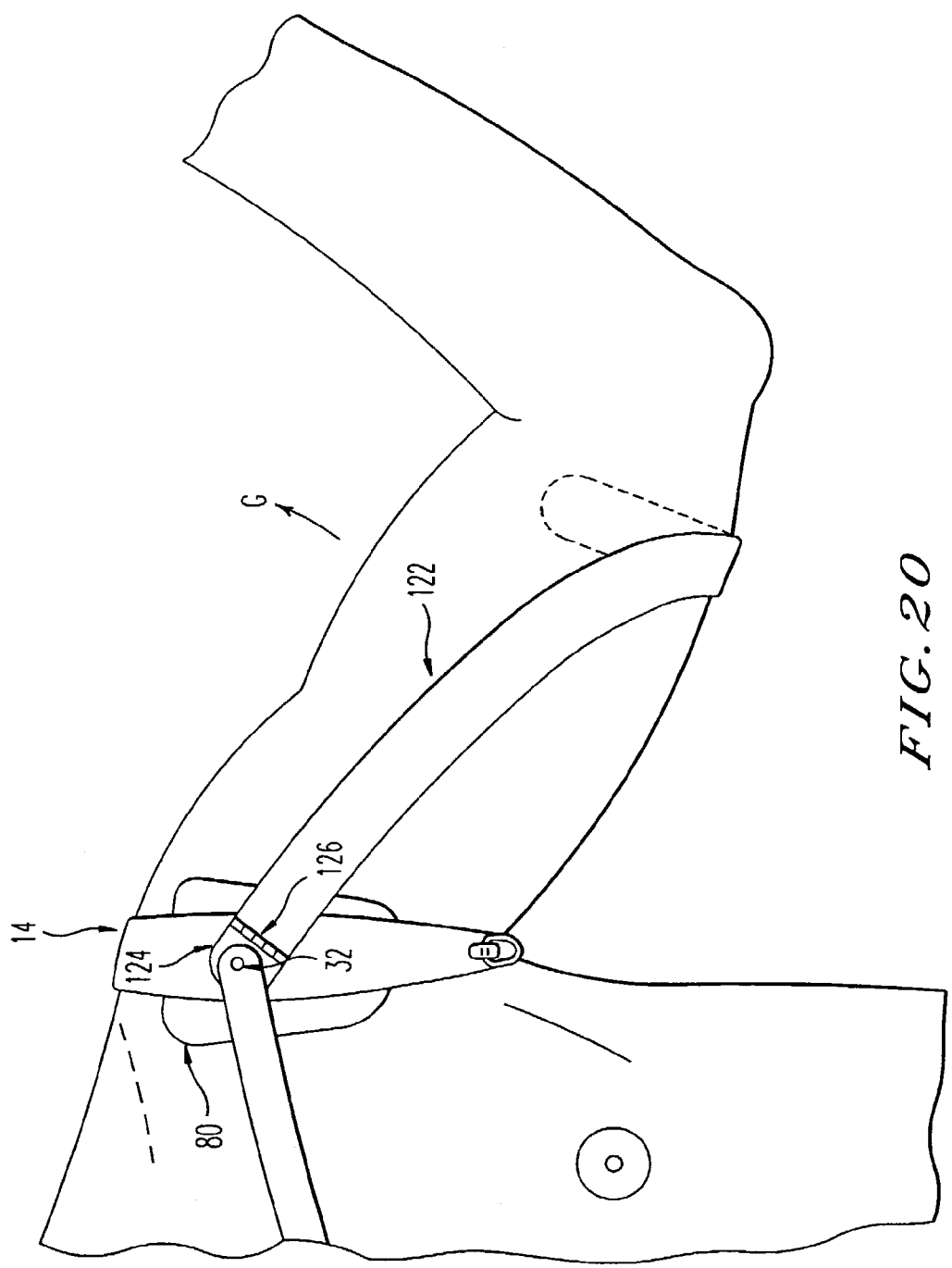
FIG. 20 is a front view of a further embodiment of the shoulder brace of the present invention.
Figure 21:
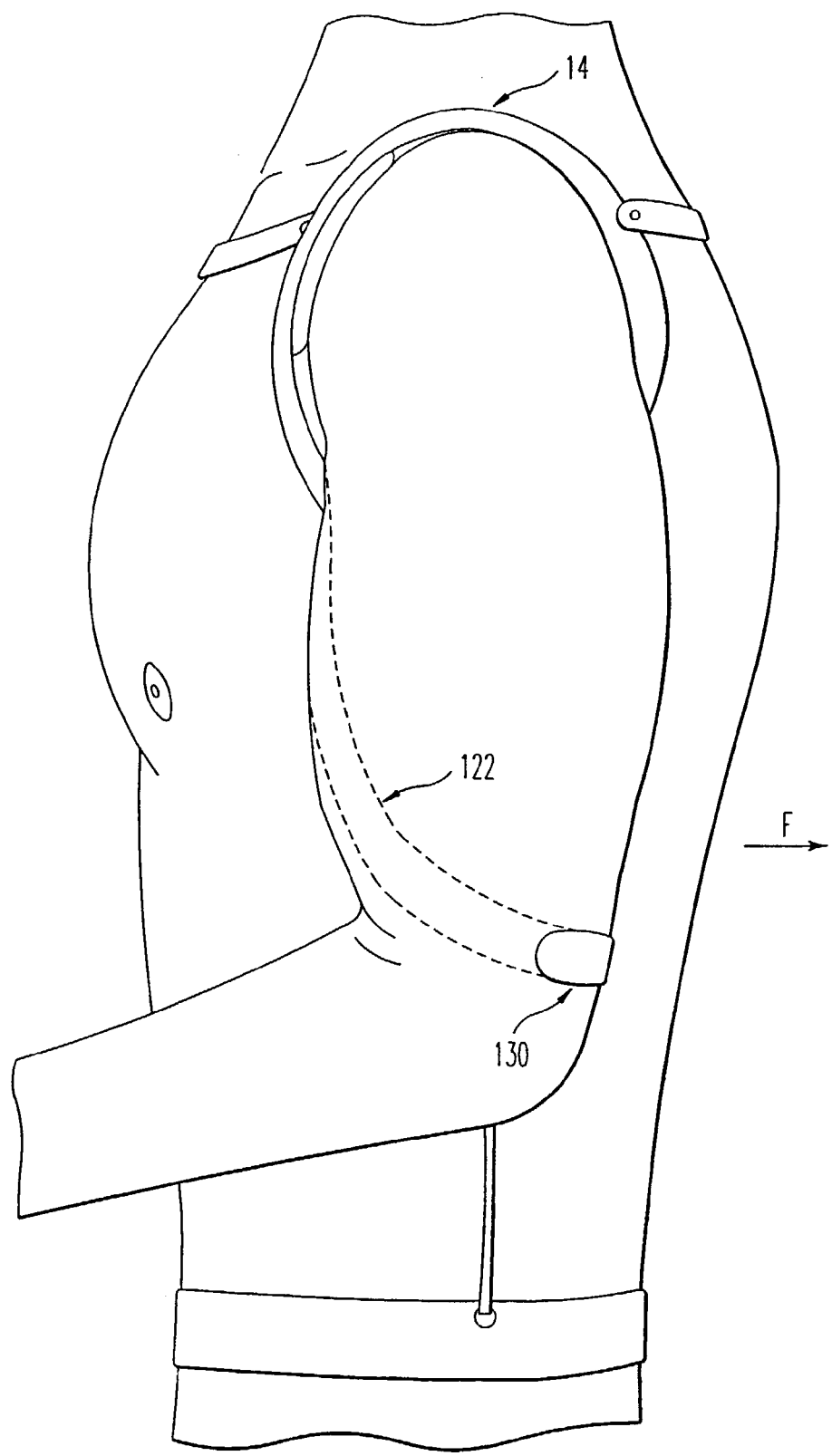
FIG. 21 is a side view of the embodiment shown in FIG. 20.

FIG. 16 illustrates a further alternative embodiment to the present invention. In this embodiment, the shoulder brace is provided with limiter 122 which is attached to alignment pivot plate 124 which is in turn pivotally mounted to pivot 32. Limiter member 122 extends downwardly from hinge 126 the patient's upper arm, curls along an inside surface 128 of a patient's arm then behind the elbow of the patient's arm at an elbow end 130 of limiter member 122. Limiter member 122 is preferably made of a semi-rigid material which can flex with movement of the user but provides, however, a desired amount of resistance to specified motions. For example, with the configuration as described above, limiter member 122 will provide strong resistance to the movement of the patient's arm in a rearward direction along arrow F shown in FIG. 21. However, because limiter member 122 is hinged to alignment plate 124, which is in turn pivotally attached to shoulder joint member 14, limiter member 122 can freely rotate around pivot 32 so that a movement of the patient's arm in the direction of arrow G, as shown in FIG. 20, is not excessively resisted. Hinge 126 also allows a user to move their arm in adduction without excessive impingement. For example, if a user moves their arm from the position shown in FIG. 20 by moving the arm shown so that the elbow moves towards the patient's chest, hinge 26 will allow limiter member 122 to rotate around hinge 126 and thereby allow the patient's arm to move in adduction. Also as shown in FIG. 16, alignment strap 16 is constructed with a telescoping portion 132. Telescoping portion 132 includes a tongue element 134 and the sleeve element 136. Sleeve element 136 is hingedly attached to alignment plate 124 with telescope hinge 138. Constructed as such, the telescoping portion provides greater mobility in that when the shoulders of the patient are shrugged forward, the telescoping portion can contract and sleeve element 136 can rotate around telescope hinge 138 so that impingement is prevented. This provides greater comfort for a user. Sleeve element 136 may optionally include a biasing device (not shown) such as a spring to bias tongue element 134 into sleeve element 13.

Figure 17:
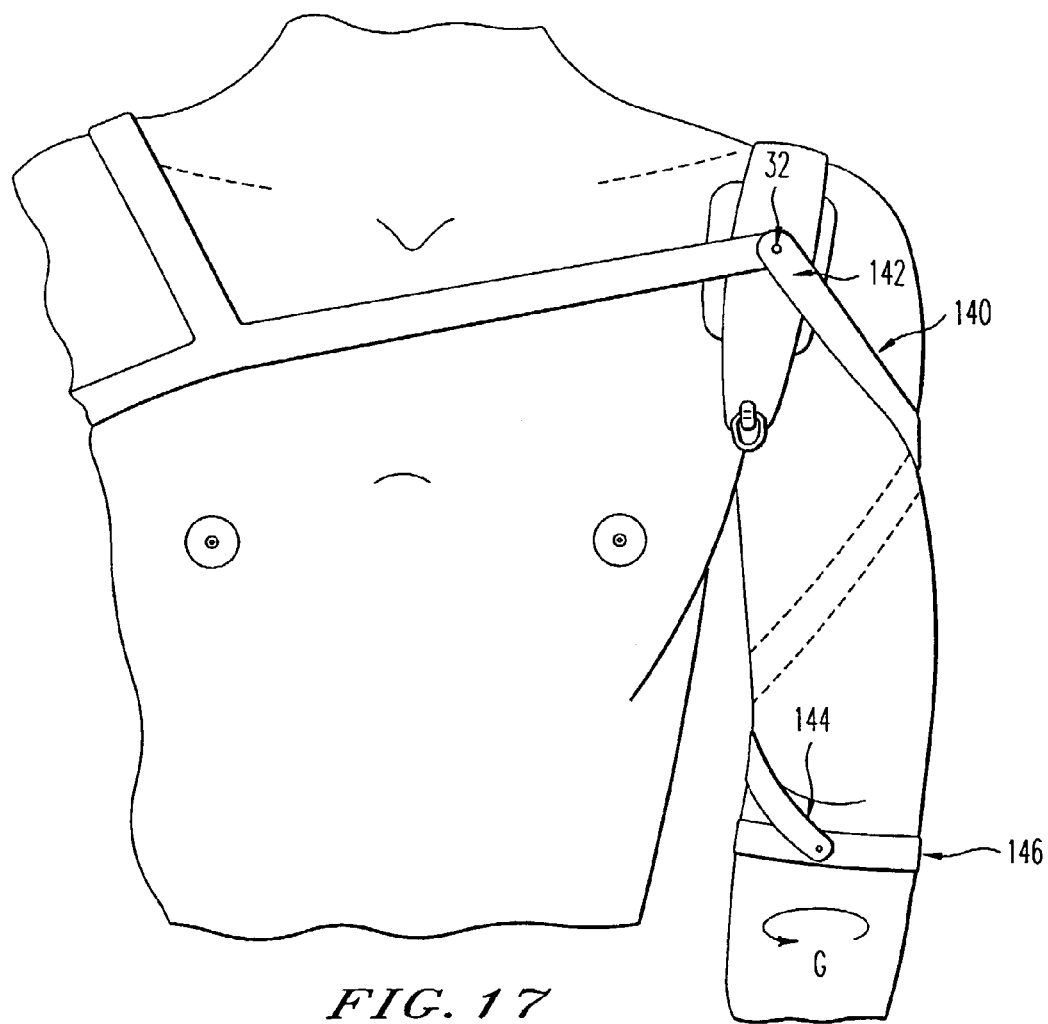
FIG. 17 is a further embodiment of the shoulder brace of the present invention.
Figure 18:
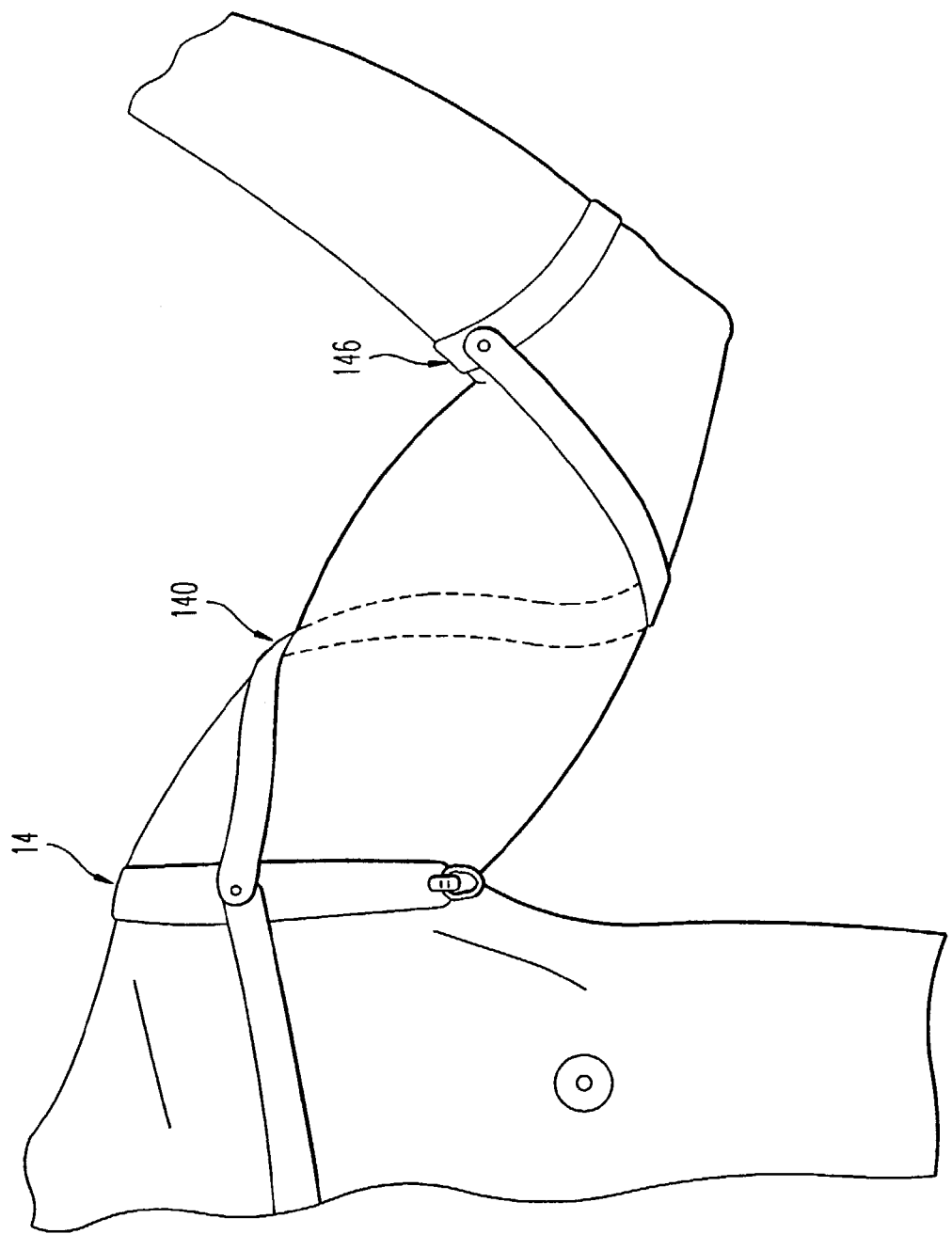
FIG. 18 is an additional side view of the embodiment shown in FIG. 17 according to the present invention.
Figure 19:
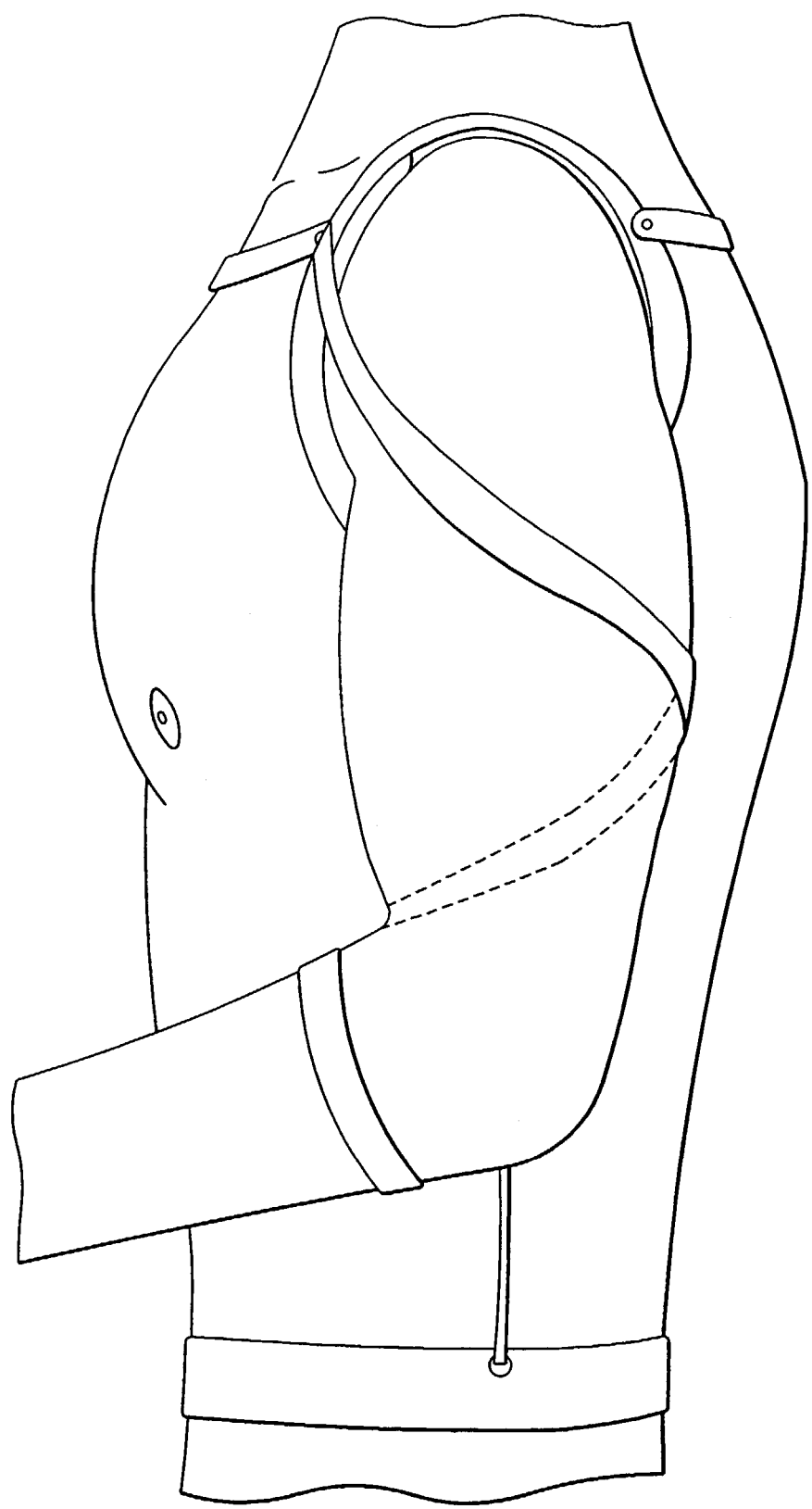
FIG. 19 is a side view of the embodiment shown in FIG. 18.

Referring now to FIG. 17, a further embodiment of the present invention is shown therein. As shown in the figure, the shoulder brace is provided with an anti-rotation strap which is wound helically around the upper arm of the patient with at least one turn. Upper end 142 of anti-rotation strap 140 is pivotally connected to pivot 32 and lower end 144 of anti-rotation strap is connected to anti-rotation anchor 146. Arranged as such, anti-rotation strap 140 resists rotation of the patient's arm in the direction of arrow G as shown in FIG. 17. However, anti-rotation strap 140 does not inhibit upward motion of the patient's arm as shown in FIG. 18.

Figure 22:
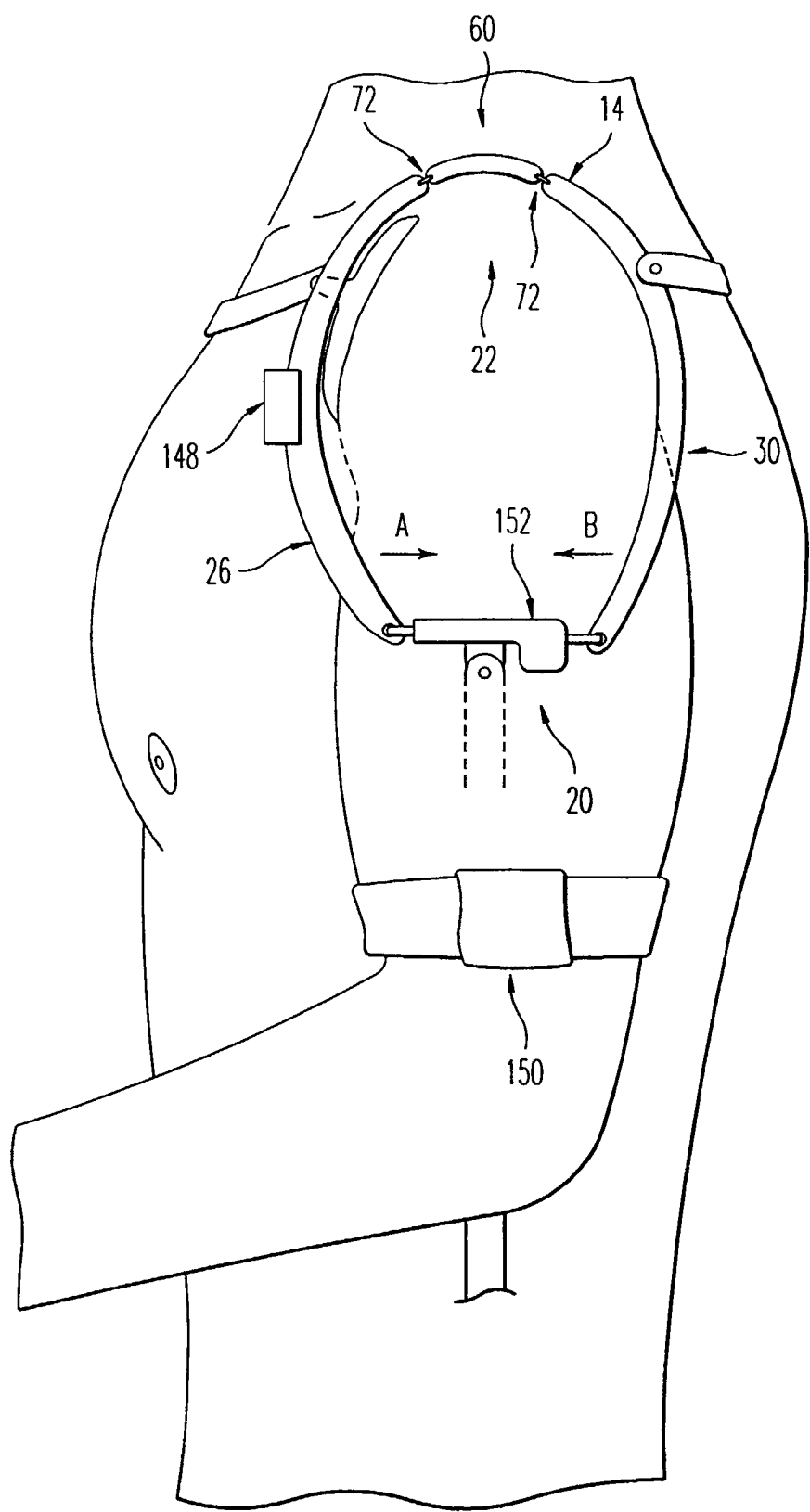
FIG. 22 is a side view of a further embodiment of the shoulder brace according to the present invention.

A further embodiment of the present invention is shown in FIG. 22. As shown in this figure, positioning device includes a reference orientation detecting device 148, an arm orientation detecting device 150 and a compression device 152. Orientation detecting devices 148 and 150 can be constructed of inclinometers, for example. In this embodiment, compression device 152 is configured to pull front arm 26 and rear arm 30 in a direction of arrows A and B respectively, when the patient's arm is moved into a "danger zone". Compression device 152 may be constructed of a solenoid or other electronic or hydraulic device. In operation, orientation detecting device 148 can provide a signal corresponding to the orientation of the patient's shoulder since shoulder joint member 14 remains relatively stationary with respect to the patient's shoulder joint 22. Orientation detecting device 150 provides a signal corresponding to the orientation of the patient's upper arm. In this embodiment, a comparator (not shown) which may be incorporated into orientation detecting device 150 or 148, or into compression device 152, compares the orientation signals output by orientation detecting devices 148 and 150 and determines if the patient's arm is in a danger zone. If the patient's arm is in a danger zone, then the comparator signals compression device 152 to compress front arm 26 and rear arm 30 of shoulder joint member 14 in the directions of arrows A and B respectively. In this embodiment, it may be preferable to incorporate hinges 72 into flexible portion 60 so as to minimize resistance to the compression caused by compression device 152 since any resistance will require additional power to be supplied to compression device 152, and therefore require additional weight. This embodiment is also particularly useful for patient's who have experienced an extreme injury or disability. Since this embodiment does not rely on any motion of the patient's arm to provide energy for compressing or releasing the anterior-posterior compression of the patient's shoulder joint, there is no inhibition of the patient's arm movements. Therefore, this embodiment allows for maximum movement of the patient's arm and therefore aids the patient in the movements that may be required in physical therapy.

Figure 23:
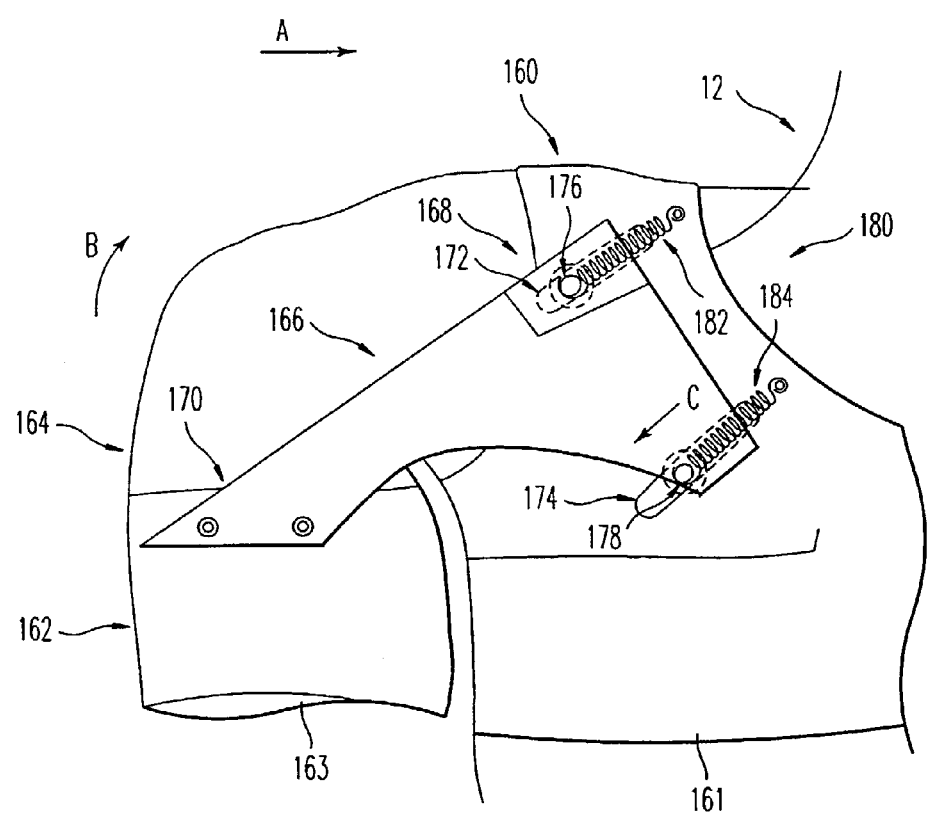
FIG. 23 is a front view of a further embodiment of the shoulder brace of the present invention.

Referring now to FIG. 23, a further embodiment of the present invention is constructed of a first mounting member 160 configured to fit over at least a pectoral area of a user or patient 12. A second mounting member 162 is configured to be mountable to an upper arm portion 164 of a patient's arm. First mounting member 160 may be constructed out of any material. However, it is preferable that first mounting member 160 is made from at least a semirigid material such as plastic or even light metals such as aluminum. Preferably, only a portion of first mounting member 160 is made from a rigid material, so as to avoid impingement upon the user's skin. The remaining portion 161 of first mounting member 160 could be made from spandex or other materials so as to provide maximum comfort. Second mounting member 162 may also be made of an at least a semirigid material such as plastic or light metals. Similarly, the portion of second mounting member 162 made from the at least semirigid material is preferably made as small as possible, while the remaining portion 163 of second mounting member 162 is made from a fabric so as to maximize comfort.

As shown in FIG. 23, a connecting member 166 is attached to a first mounting member 160 at a first end 168 and is attached to second mounting member 162 at a second end 170.

Also shown in FIG. 23, are two parallel slots 172 and 174 formed in first mounting member 160. First end 168 of connecting member 166 is slidably connected to slots 172 and 174 via mounting members 176 and 178. Optionally, mounting members 176 and 178 may include threaded fasteners (not shown) for anchoring the connection between the first end 168 of connecting member 166 to first mounting member 160. This allows a user to install the shoulder brace in such a way so as to immobilize the patient's shoulder, which may be desirable immediately after an injury, for example.

As shown in FIG. 23, positioning device 180 is formed of two springs 182 and 184 which bias the connecting members towards a medially inward direction, i.e., in the direction of arrow A shown in FIG. 23. By construction of the shoulder brace as such, a patient's weakened glenohumeral ligaments, which may have been weakened by a dislocation injury, are prevented from being stressed by the medially inward bias created by the positioning device 180. Although not illustrated in FIG. 23, positioning device 180 may be formed with a single slot and/or a single spring.

One advantage of forming the shoulder brace with slots 172 and 174 and springs 182 and 184, is that when a user rotates their upper arm 164 in the direction of arrow B, mounting member 178 is pushed in the direction of arrow C, thereby adding tension into spring 184, thereby causing additional medially inward pressure, thereby preventing stress being imparted to the glenohumeral ligaments.

As shown in FIG. 23, connecting member 166 is in the form of a plate. Preferably, connecting member 176 is made from a semirigid material that allows some flexation, so that a patient may have some mobility. However, for certain injuries, it may be desirable to construct a connecting member 166 from a rigid material having a thickness which would prevent movement of the user's upper arm 164 forward or backwards. On the other hand, by constructing connecting member 166 from a more flexible material, such as a hard rubber, the patient or user is not preventing from moving their upper arm 164 forward or backward, and is thereby provided with some flexibility.

Additionally, the shoulder base may include a second connecting member (not shown) configured to be arranged in essentially an identical configuration shown in FIG. 23, but arranged on the user's back. By adding an additional connector member 166 as such, the shoulder brace provides additional support and symmetry to the forces imparted to the shoulder joint.

Figure 24:
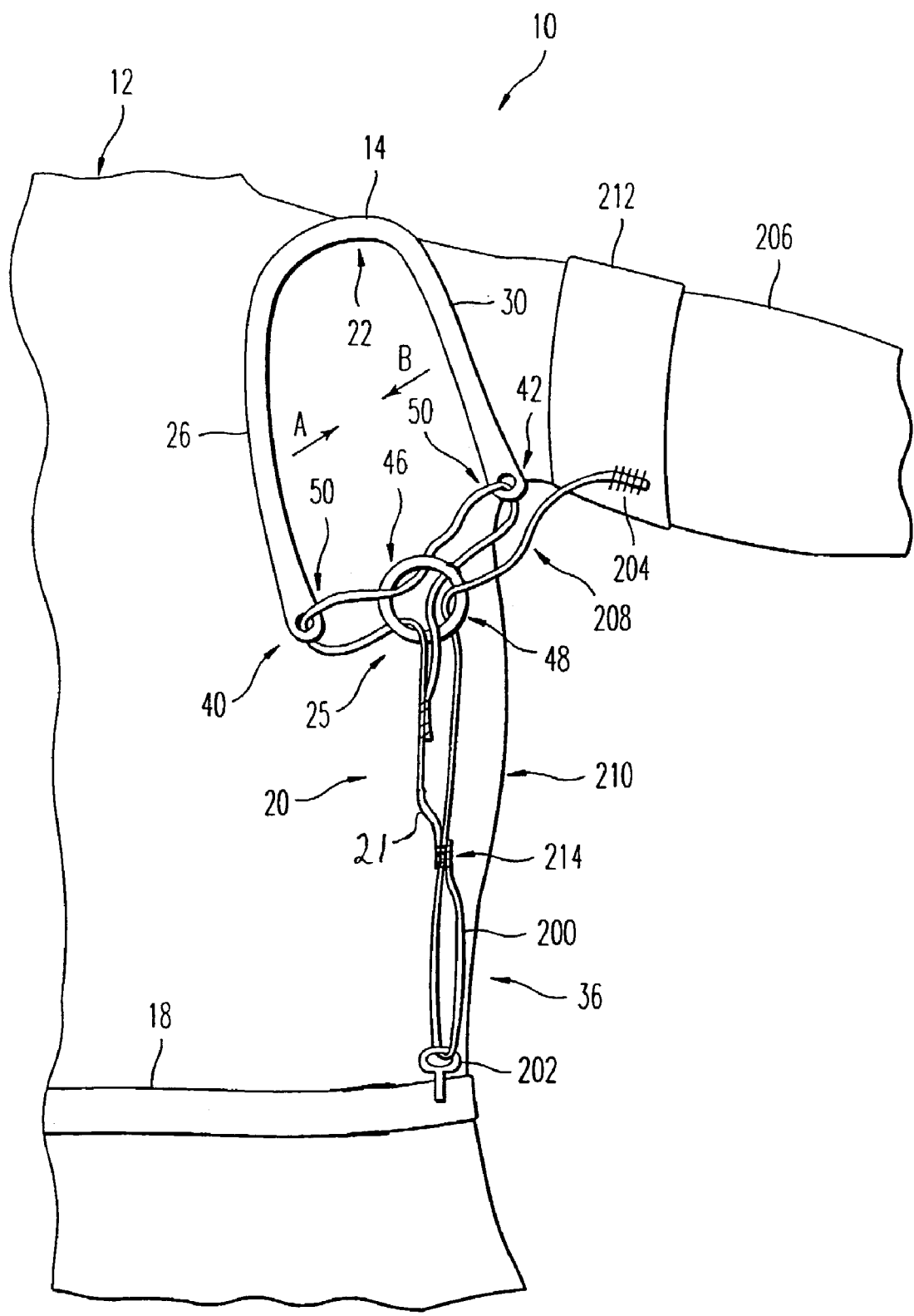
FIG. 24 is a front view of a further embodiment of the shoulder brace of the present invention.
Figure 25:
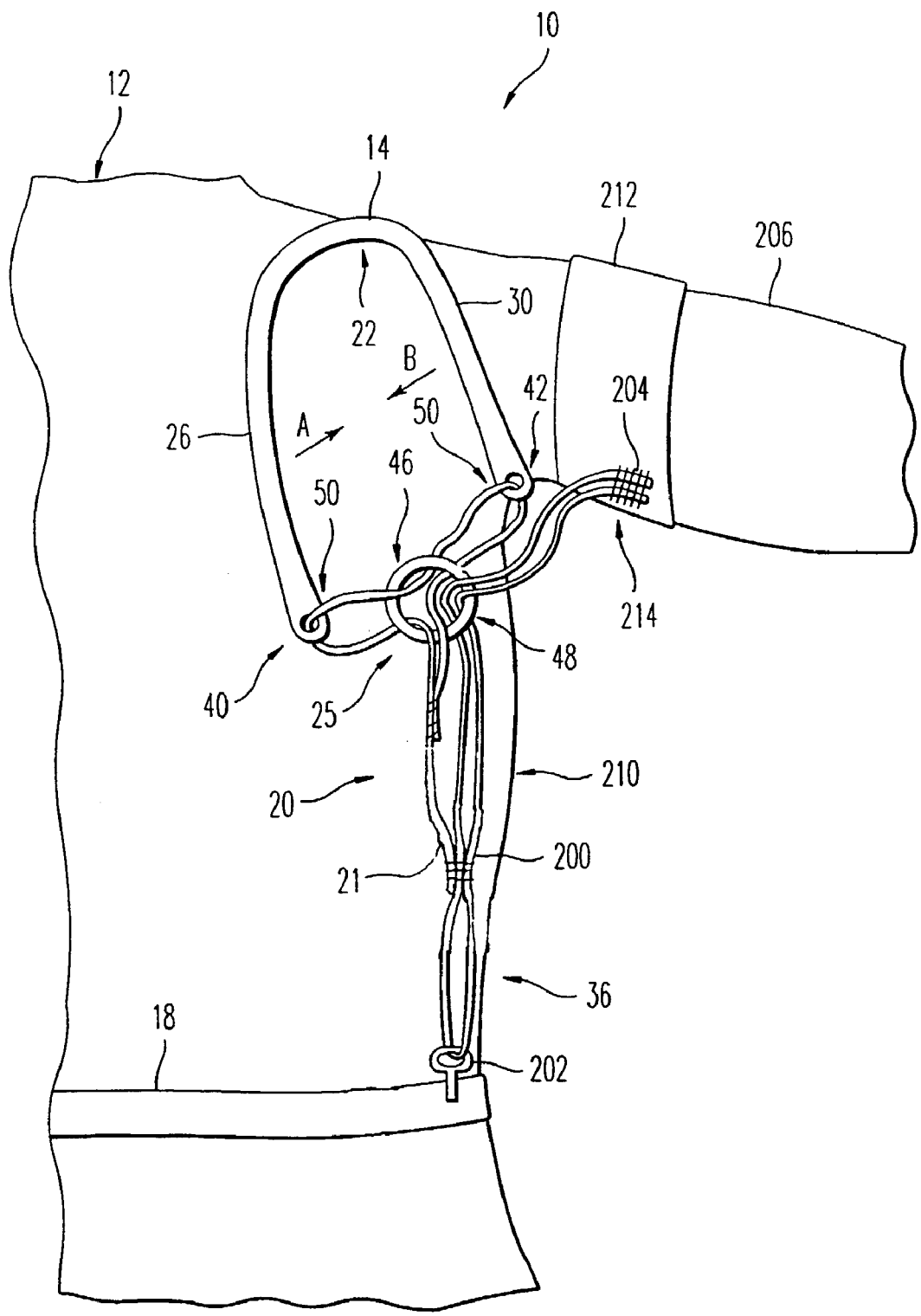
FIG. 25 is a front view of a further embodiment of the shoulder brace of the present invention.

FIGS. 24 and 25 illustrate other embodiments of the shoulder brace of the present invention. The shoulder braces shown in FIGS. 24 and 25 are similar to that shown in FIGS. 1 and 2, for example, but the positioning unit 20 includes at least one additional tension triggering strap 200. The elements shown in FIGS. 24 and 25 which have the same reference numerals as in FIGS. 1-23 are not described for simplicity purposes. However, it is to be noted that any of the shoulder braces previously discussed and shown in the Figures may be used with the additional tension triggering strap 200.

FIG. 24 illustrates the tension triggering strap 200 connected to an arm band 212 on an upper arm portion 206 of the patient 12. The tension triggering strap 200 is passed through the tensioner ring 46 and looped through a ring 202 attached to the anchor strap 18. One end 204 of the tension triggering strap is attached to the arm band 212. The one end 204 may be riveted, clamped, sewn, etc., so that the one end 204 is fixedly secured to the arm band 212. Further, the arm band 212 is placed as close to an armpit of the user so that a shirt may be easily placed over the shoulder brace 10 including the tension triggering strap 200. Another end 214 of the tension triggering strap 200 is looped through the ring 202 and then attached to the strap 200 with a binder, for example (similar to the binder 58 discussed in FIGS. 1 and 2, for example). Further, the tension triggering strap 21 is also fixed at the end 214 of the tension triggering strap 200. Threaded as such, the strap 200 is guided through the tensioner ring 46 such that when the strap 200 is provided with tension when a patient wearing a shoulder brace 10 raises their arm, the positioning device 20 contracts shoulder joint member 14 such that the front arm 26 of the shoulder joint member 14 is compressed towards rear arm 30 so as to cause an interior-posterior compression of the shoulder joint. The tension triggering strap 200 provides additional compression of the front arm 26 towards the rear arm 30 indicated by arrows A and B.

The shoulder brace 10 shown in FIGS. 24 and 25 may also include alignment straps, such as an alignment strap 16 shown in FIGS. 1 and 2. In addition, the anchor strap 18 is shown wrapped around a patient's torso 36. However, the anchor strap 18 may be positioned according to the preferences of the patient. In addition, the anchor strap 18 may alternatively be provided approximately around the midriff, thigh or hips, for example. That is, the anchor strap 18 may be placed at a most comfortable position for the patient and which provides a sufficient tension for the triggering straps 21 and 200.

The ring 202 may be secured to the anchor 18 by sewing, a binder, glue or may be omitted. That is, the strap 200 may be looped through a hole provided in the anchor 18. Alternatively, the triggering strap 200 may be fixedly secured to the anchor 18 in a similar fashion as the triggering strap 21.

FIG. 25 is similar to FIG. 24 but the first and second ends 204 and 214 of the triggering strap 10 are attached (e.g., fixedly secured) to the arm band 212. In addition, FIG. 25 illustrates two portions of the strap 200 passing through the tensioner ring 46, whereas FIG. 24 illustrates only one portion of the strap 200 passing through the tensioner ring 46.

In addition, the lengths of the straps 21 and 200 may be varied by using clamps rather than glueing or sewing the ends 204 and 214 (in both of FIGS. 24 and 25). Thus, the pressure of the shoulder brace may be adjusted by adjusting a slack in the tensioning straps 21 and 200 and clamping the ends 204 and 214 with a clamp. Further, FIGS. 24 and 25 illustrate two tension triggering straps 21 and 210. However, it is possible that these two triggering straps be included into a single tension triggering strap which performs the same functions as the two tension triggering straps.

Figure 26:
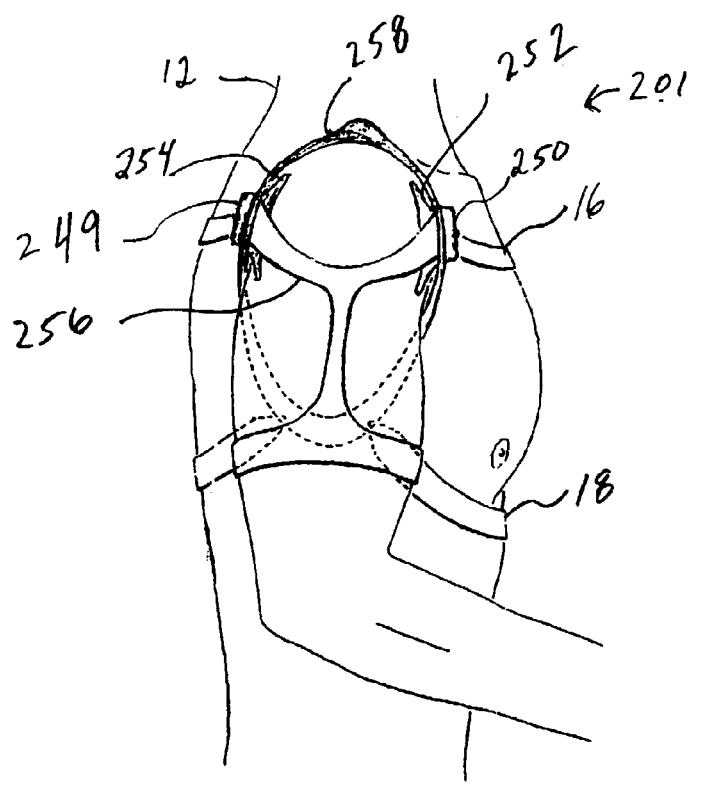
FIG. 26 is a side view of a patient wearing a further embodiment of the shoulder brace of the present invention.

FIGS. 26–29b illustrate another embodiment of the shoulder brace of the present invention. In particular, FIG. 26 illustrates the patient 12 wearing a shoulder brace 201 which includes actuators 249, 250. The actuators 249, 250 compress the shoulder joint when the patient's arm is moved. Also shown is a rigid frame which includes an arm frame member 256 and a shoulder frame member 258. The alignment strap 16 and anchor strap 18 may also be used for aligning and securing the shoulder brace 201. The straps 16 and 18 have previously been described and accordingly a detailed description is now omitted. However, note FIG. 28 (which is discussed later) illustrates an alternative arrangement for aligning and securing the shoulder brace.

Figure 27:
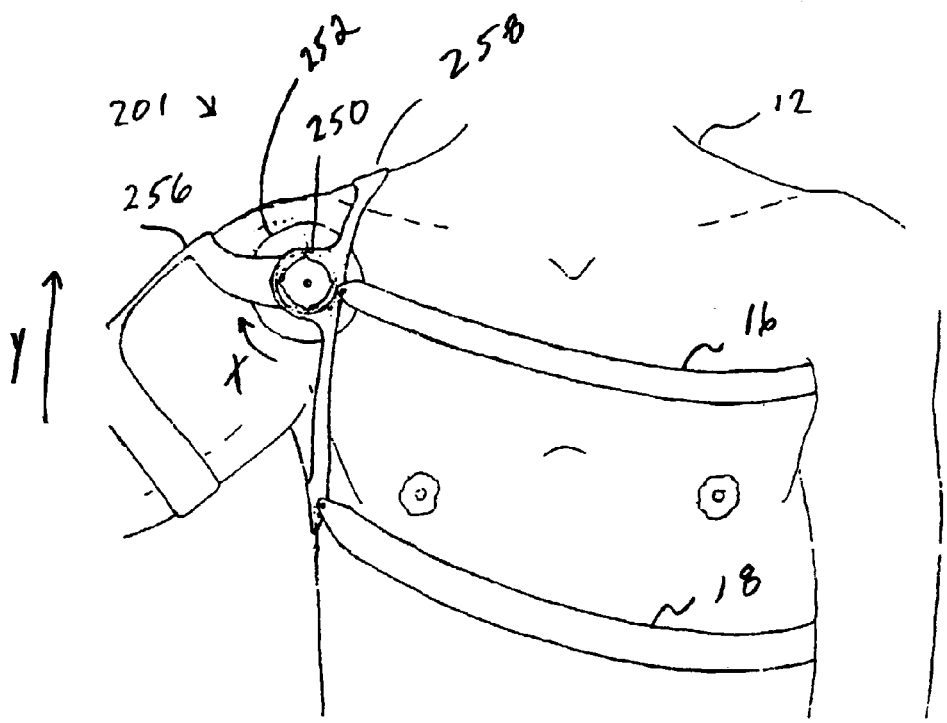
FIG. 27 is a front view of the patient wearing the shoulder brace shown in FIG. 26.

FIG. 27 illustrates a front view of the shoulder brace 201 shown in FIG. 26 and will be used to describe an operation thereof. As shown, when the right arm of the patient 12 is moved (e.g., in the direction of the arrow Y), the rigid arm frame member 256 is also moved causing a clockwise force (in the direction of the arrow X) on the actuator 250. This clockwise force causes front and rear pads 252, 254 (only the front pad 252 is shown in FIG. 27) to press against the shoulder joint of the patient 12 (and thus compress the shoulder joint). The more the arm is moved, the greater the compression force. The actuators 249, 250 are discussed in more detail with reference to FIGS. 29a–b.

Figure 28:
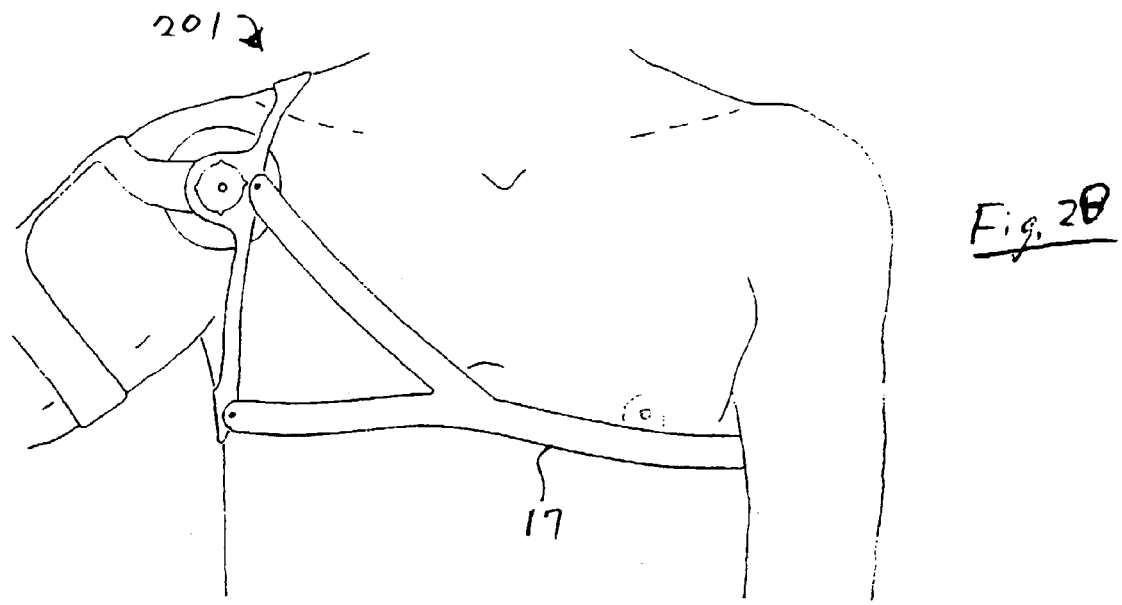
FIG. 28 illustrates an alternative alignment and anchor strap of the shoulder brace shown in FIG. 26.

FIG. 28 illustrates an alternative alignment and anchor strap 17 from the alignment strap 16 and anchor strap 18 discussed previously. As shown, the alignment strap 16 and anchor strap 18 in FIG. 27 are combined into a single strap 17 for aligning and securing the shoulder brace 201. The anchoring and alignment strap 17 reduces the number of straps and provides more comfort to the individual.

Figure 29A:
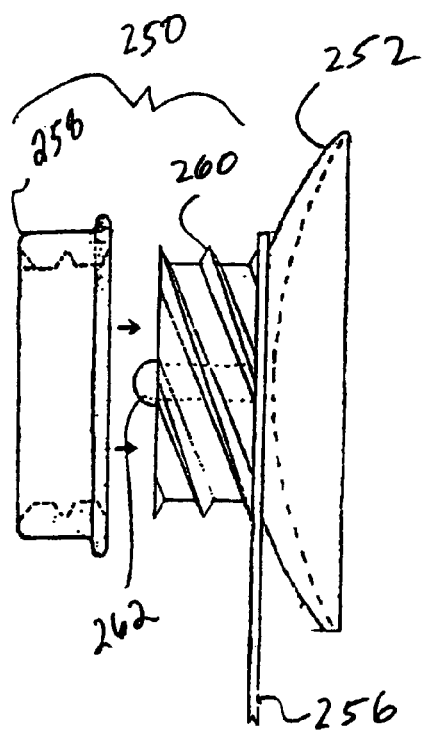
FIGS. 29a–b are cross-sectional side views of an actuating mechanism included in the shoulder brace shown in FIGS. 26 and 28.
Figure 29B:
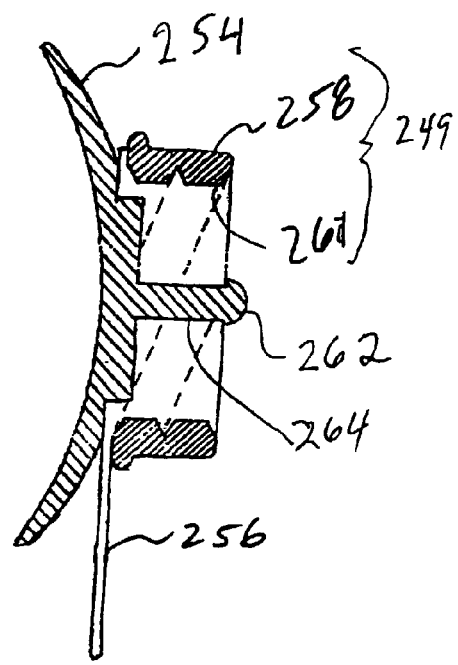

Turning now to FIGS. 29a and 29b, which are cross-sectional side views of the front and rear actuators 249, 250. In particular, FIG. 29a illustrates a disassembled view of the front actuator 250, which includes the shoulder frame member 258 threadably engaged with the frame member 256 (via a threaded portion 260). The arm frame member 256 is securely fastened (e.g., integrally molded) with the threaded portion 260, such that when the arm frame member 256 is moved away from the body, the threaded portion 260 is rotated inwards so as to press the front pressure pad 252 against the patient's shoulder joint.

In more detail, when the patient's arm is moved, the arm frame member 256 causes the threaded portion 260 to rotate such that the front pressure pad 252 presses against the patient's shoulder joint. The pressure is generated towards the patient's shoulder because the shoulder frame member 258 remains in essentially a fixed position (i.e., the frame member 258 does not move). Thus, the threaded portion 260 rotates towards the patient's shoulder joint. The rear actuator 249 operates in a similar fashion.

FIG. 29b illustrates an assembled view of the rear actuator 249 including the frame member 258 threadably engaged with the frame member 256 (via a threaded portion 261). The threaded portion 261 includes left-hand threads, whereas the threaded portion 260 includes right-hand threads, such that the threaded portions rotate inwards so as to press the front and rear pressure pads 252, 254 against the patient's shoulder joint. That is, the threaded portions 260 and 261 are oppositely threaded.

In addition, the front and rear pressure pads 252, 254 may be connected to the arm frame member 256 such that the pads do not rotate when the actuator rotates. This may be accomplished by including a projecting portion 262 of the pressure pad which freely rotates in a passageway 264 of the arm frame member 256 (see FIGS. 29a and 29b). The diameters of the projecting portions 262 are smaller than the diameters of the holes 264, and thus the pressure pads are free to rotate.

The front and rear pads 252, 254 may be assembled by pushing the projection portion 262 into the passageway 264 until the projecting portion 262 "snaps" into place, thereby securing the front and rear pressure pads 252, 254 to the frame member 256.

In addition, the frame portions may include a fiber-reinforced plastic, injected molded plastic, etc., with a sufficient rigidity to function as a frame for supporting the actuators 249, 250.

Figure 30:
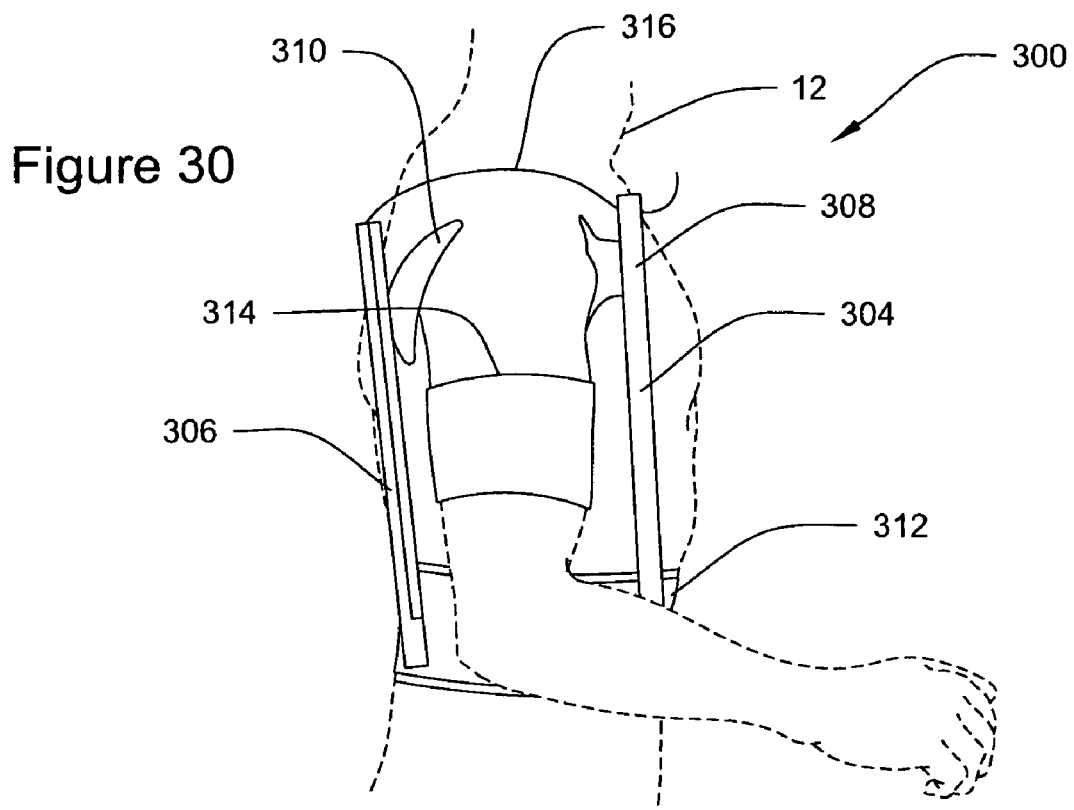
FIG. 30 is a side view of a patient wearing yet another embodiment of the shoulder brace of the present invention.

Turning now to FIGS. 30–36, which illustrate yet another embodiment of the shoulder brace of the present invention. In particular, FIG. 30 illustrates the individual 12 wearing a shoulder brace 300, which includes a front frame member 304, a rear frame member 306, a front pressure pad 308, a rear pressure pad 310, an arm cuff 314 and a support frame member 312. The front and rear pressure pads 308, 310 are respectively positioned on front and rear portions of the individual's shoulder joint and the support member 312 is positioned at a mid-section of the individual. Further, the front frame member 304 is connected to the support frame member 312 and the front pressure pad 308. Similarly, the rear frame member 306 is connected to the support frame member 312 and the rear pressure pad 310. The shoulder brace 300 also includes a cord 316 which traverses over the individual's shoulder.

Figure 31:
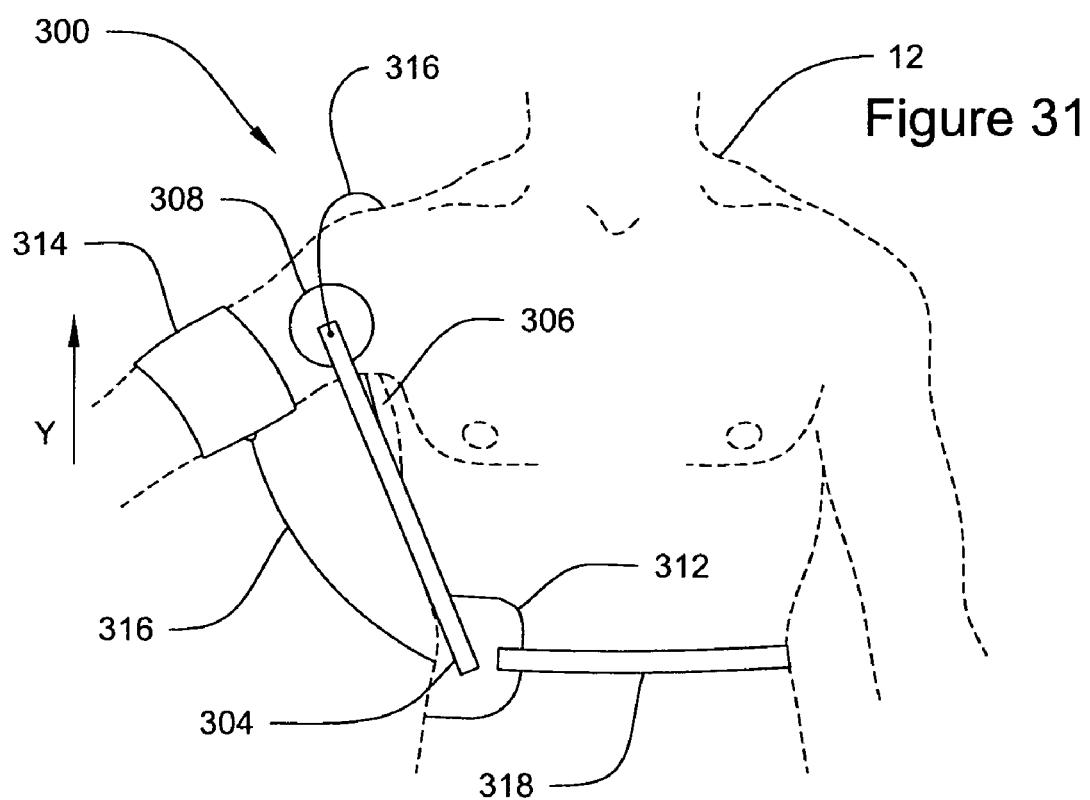
FIG. 31 is a front view of the patient wearing the shoulder brace shown in FIG. 30.

FIG. 31 illustrates a front view of the shoulder brace 300 shown in FIG. 30 and will be used to describe an operation thereof. As shown, when the right arm of the individual 12 is moved away from the body (e.g., in the direction of the arrow Y), the arm cuff 314 is also moved, which pulls the cord 316. This causes the compression mechanism (described in more detail later) to compress the front and rear frame members 304, 306 in accordance with the movement of the individual's arm such that the front and rear pressure pads 308, 310 press against the individual's shoulder joint. The more the arm is moved, the greater the compression force. Also shown in FIG. 31 is an anchor strap 318 for securing the support frame member onto the mid-section of the individual. The anchor strap 318 may be a nylon belt, for example.

Figure 32:
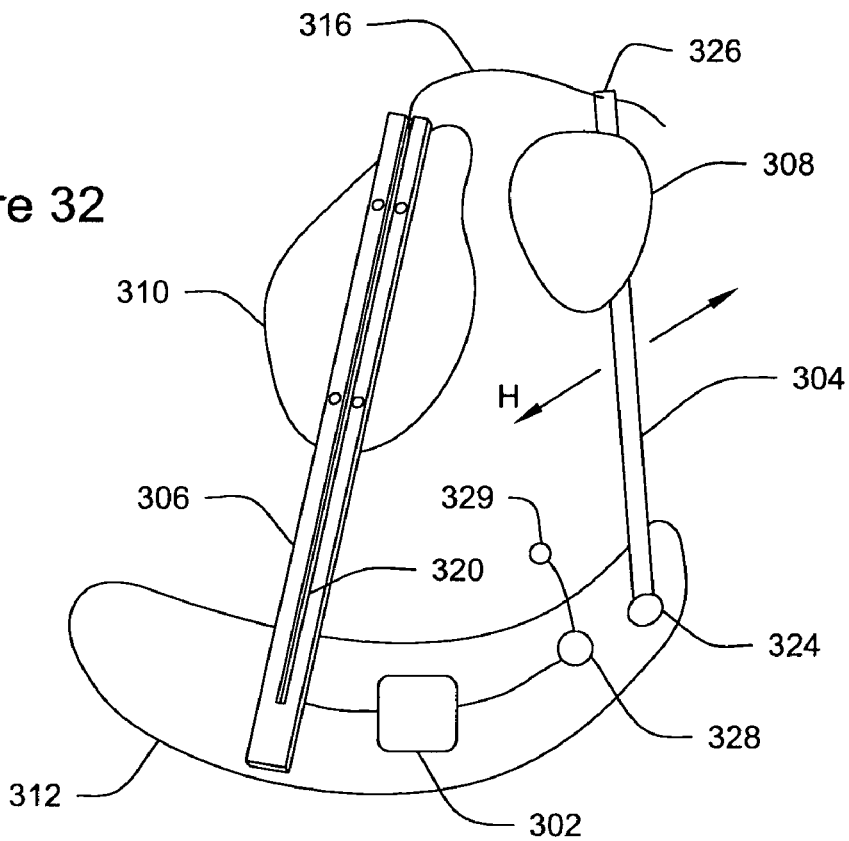
FIG. 32 is a schematic of a compression mechanism included in the shoulder brace shown in FIGS. 31 and 32.

Turning now to the different examples of the compression mechanisms according to the present invention. In the first example, as shown in FIG. 32, the compression mechanism includes a gear box 302 connected to the support frame member 312. In addition, the cord 316 is routed from an anchor point 329 on the arm cuff (not shown) through the gear box 302, onto a surface of the rear frame member 306, over the individual's shoulder, and onto an anchor point 326 on the front frame member 304.

Thus, according to this example, the cord 316 is pulled so as to compress the front and rear frame members 304, 306 in accordance with the movement of the individual's arm such that the front and rear pressure pads 308, 310 press against the individual's shoulder joint. The gear box 302 (shown in more detail in FIG. 36) provides the efficient conversion ratio (e.g. a 4:1 gear ratio or any other gear ration necessary to achieve to amount of pressure required to compress the shoulder joint) so that the further movement of the individual's arm away from the body results in a greater compression force.

Further, a plurality of pulleys may be positioned along the route of the cord 316 so as to facilitate the easy movement of the cord 316. For example, in FIG. 32, a pulley 328 is provided on the support member 312 so as to facilitate the easy movement of the cord between the gear box 302 and the arm cuff 314. Also shown is a cord anchor 326 for anchoring the cord 316 onto the front frame member 304. In addition, the rear frame member includes a groove 320 for receiving and routing the cord 316 along the surface of the rear frame member 306. Note, a plurality of pulleys may also be positioned along the rear frame member to facilitate a movement of the cord. For example, the cord 316 may be anchored by passing it through a plurality of hole in the frame member and securing an end of the cord through at least one loop created by the cord passing in and out of the plurality of holes. Another method of securing the cord is by using a screw and washer type mechanism to secure fasten the cord to the frame member.

Figure 33:
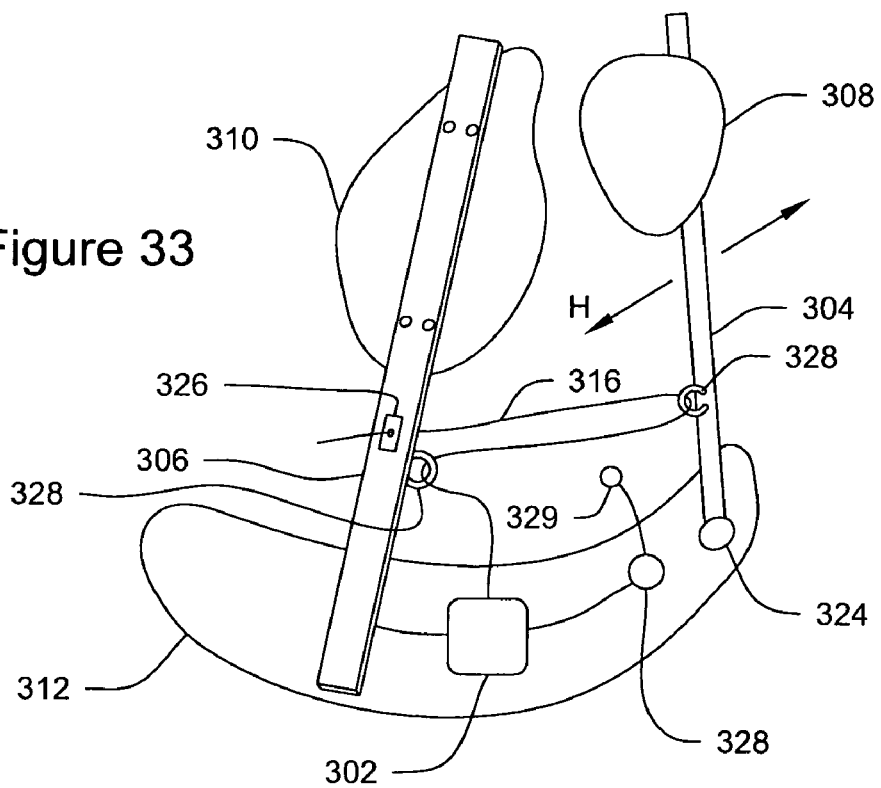
FIG. 33 is a schematic of another compression mechanism included in the shoulder brace shown in FIGS. 31 and 32.

Turning now to FIG. 33, which illustrates another example of the compression mechanism according to the present invention. As shown, the cord 316 is routed from an anchor point 329 on the arm cuff (not shown), through the gear box 302, onto a pulley 328 included on the rear frame member, under the individual's shoulder (note this differs from FIG. 32 in which the cord 316 is routed over the individual's shoulder), through a pulley 328 included on the front frame member 304, and back under the individual's shoulder to an anchor point 326 on the rear frame member 306. Thus, as the individual's arm is moved, the cord 316 is pulled so as to compress the front and rear pressure pads 308, 310 against the individual's shoulder joint. Note the rear frame member 306 in FIG. 33 does not include a groove as in FIG. 32.

Figure 34:
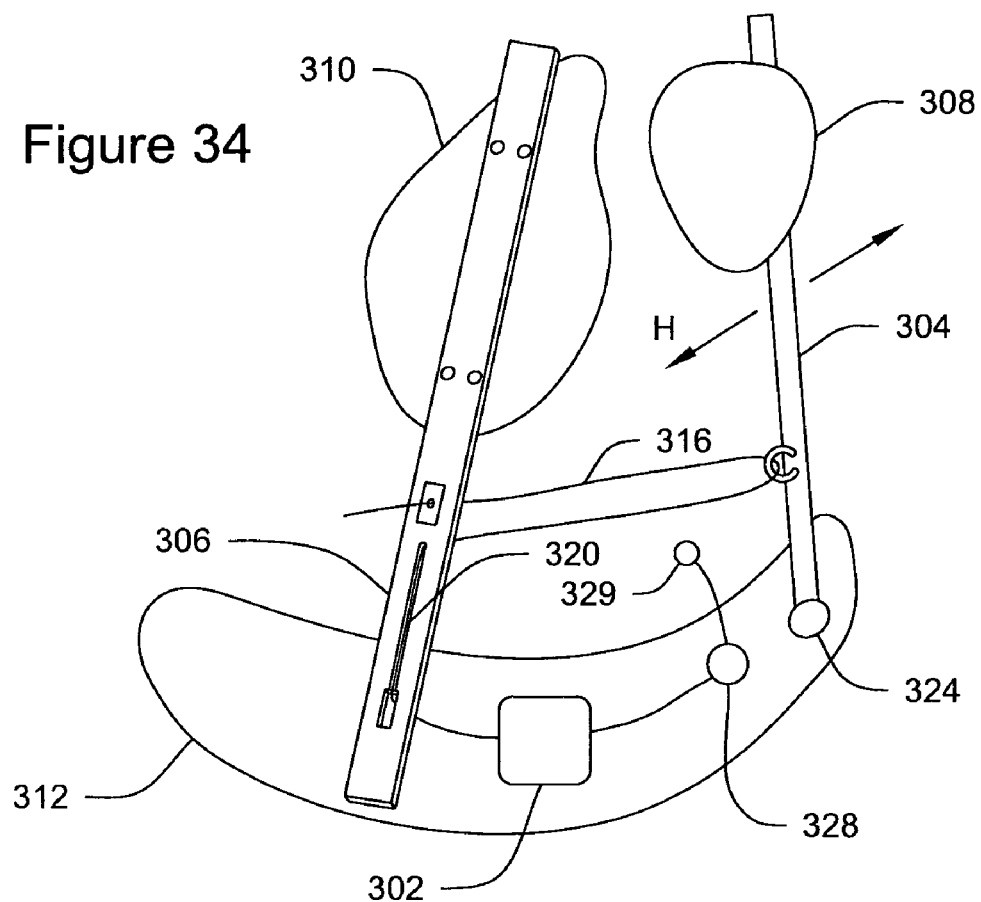
FIG. 34 is a schematic of yet another compression mechanism included in the shoulder brace shown in FIGS. 31 and 32.

FIG. 34 illustrates yet another example of the compression mechanism according to the present invention. Note FIG. 34 is similar to FIG. 33, except the cord 316 is routed from the anchor point 329 on the arm cuff (not shown), through the gear box 302, onto a surface of the rear frame member 306 through the groove 320, under the individual's shoulder to a pulley 328 included on the front frame member 304, and back under the individual's shoulder to an anchor point 326 included on the rear frame member 306. Thus, as the individual's arm is moved, the cord 316 is pulled so as to compress the front and rear pressure pads 308, 310 against the individual's shoulder joint.

In addition, it is also possible to not loop back the cord 316 under the individual's shoulder. That is, the cord 316 may be anchored onto the front frame member 304. However, looping the cord 316 between the front and rear frame members 304, 306 provides an additional compression force.

In addition, the front pressure pad 308 is moveably connected to the front frame member 304 (e.g., via a ball and socket type connection) and may be "snapped" onto the front frame member 304. The front pressure pad 308 may be movable to accommodate movement of the individual's front shoulder joint. That is, the front shoulder joint tends to move more than the rear shoulder joint when the individual's arm is moved. Alternatively, both the front and rear pressure pads 308, 310, may be movably connected to, or permanently fixed to, the front and rear frame members 304, 306.

Further, as shown in FIGS. 32–34, the front frame member 304 is pivotably connected to the support frame member 312 at an end thereof (i.e., pivoted about a pivot joint 324 in a direction of the arrow H).

Figure 36:
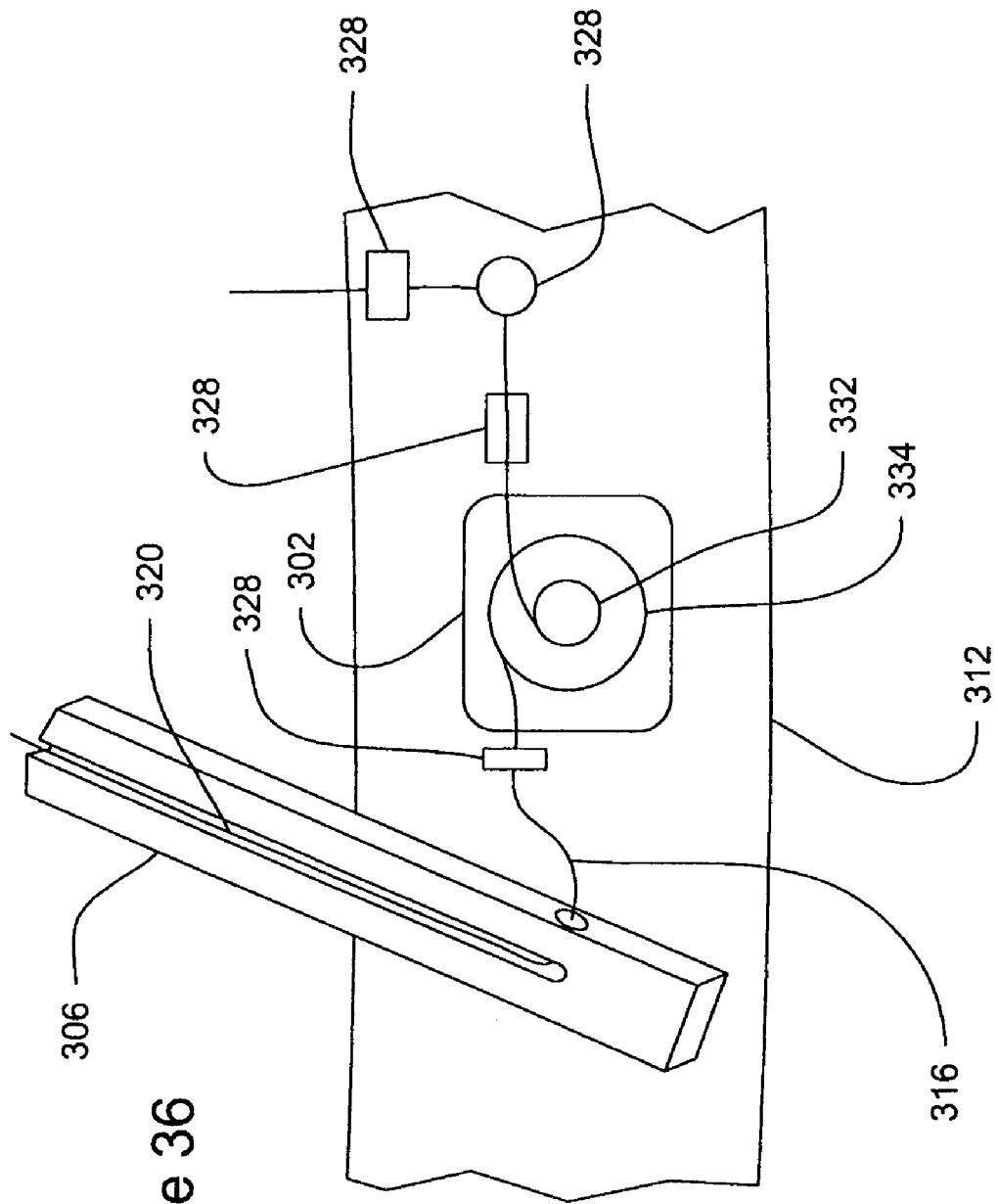
FIG. 36 is a schematic illustrating a gear box included in the compression mechanism according to the present invention.

FIG. 36 illustrates an adjustment mechanism configured to adjust the location of the rear pad 310 on the individual's shoulder joint. For example, as shown, the rear frame member 306 and the support member 312 include slots 336, 338 at an interconnection region thereof such that the positioning of the rear pressure pad 310 on the individual's shoulder joint may be adjusted. Also shown are fasteners 340 (e.g., a nut and bolt) used to lock the rear frame member 306 into the desired adjustment. Thus, the rear frame member may be set into a desired position so as to set the position of the rear pad 310 on the individual's shoulder joint. The front and rear pads 308,310 may also be adjusted on the front and rear frame members 304 and 306, respectively.

In addition, the arm cuff 314 may be made from a rigid plastic material and include a velcro portion so as to be easily positioned and secured to the arm of the individual. For example, the arm cuff 314 may be placed around the individual's arm and then secured via the velcro strap.

In addition, the support frame member 312 may be made from a rigid plastic material such as polystyrene, the front and rear frame members may be made from a rigid lightweight metal, such as aluminum, and the front and rear pads and the arm cuff 314 may be made from a rigid plastic material (such as polystyrene) including a thermoplastic padding to provide comfort and to provide location stability. The material selected for the shoulder brace should provide the sufficient rigidity required and be lightweight. The cord material may be a braided cord having sufficient strength to withstand the tensions to compress the front and rear frame members 304, 306 in accordance with the movement of the individual's arm (such as a braided cord manufactured by Western Filament under the trademark SPECTRA).

Figure 35:
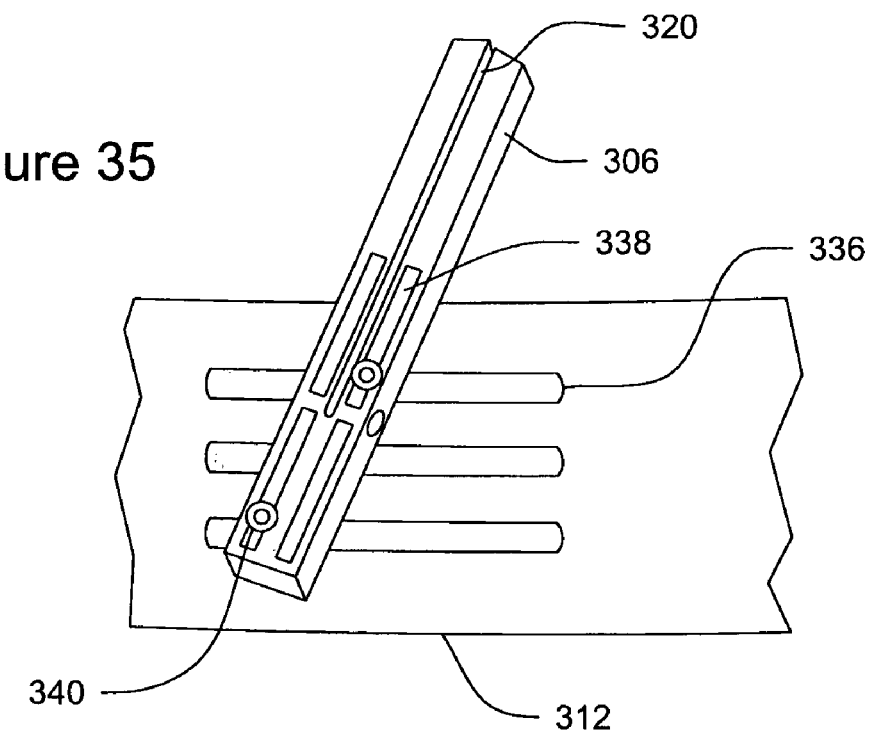
FIG. 35 is a schematic illustrating an adjustment mechanism for a rear frame member of the shoulder brace according to the present invention.

Turning now to FIG. 35, which illustrates the gear box 302 in more detail. As shown, the gear box 302 includes a first wheel 332 and a second wheel 334 attached to the first wheel 332. Note, the first and second wheels 332, 334 may be a single component (e.g., be integrally molded). The second wheel 334 has a larger diameter than the diameter of the first wheel 332. Thus, because the second wheel 334 has a larger diameter than the first wheel 332, a larger pulling force on the front and rear frame members 304, 306 is created with a movement of the individual's arm. That is, the gearbox 302 converts the pulling force created by the movement of the arm cuff 314 into a larger pulling force (e.g., a pulling force which is 4 times greater) used to pull the front and rear members 304, 306 together.

In addition, as shown, the cord 316 is routed from the arm cuff (not shown) through the pulleys 328 provided on the support frame member 312 into the gear box 302 and is wound around (at least once) the first and second wheels 332, 334. The cord 316 then exits the gear box 302 and is routed over a pulley 328 into the rear frame member 306 (via a through hole) and onto the groove 320 of the rear frame member 306. The cord 316 may be a single cord as shown in the figures, or may be, for example, two separate cords: a first cord connected to the first wheel 332 and a second cord connected to the second wheel 334.

Thus, according to the present invention, a shoulder injury may be efficiently treated via the shoulder brace shown in the FIGS. 30–36 by positioning the front and rear pressure pads on front and rear portions of the individual's shoulder joint, positioning the shoulder member at a mid-section of the individual, and positioning the arm cuff on the arm of the individual. Then, the compression mechanism compresses the front and rear frame members in accordance with a movement of the individual's arm such that the front and rear pressure pads press against the individual's shoulder joint. The positions of the front and rear pads may also be adjusted and the support frame member may be secured to the mid-section of the individual.

Further, because wounds may appear or be at locations where the shoulder brace contacts the individual's skin (e.g., at the front and rear pressure pads, on the inner surface of the arm cuff, etc.), a bacteria static material may be applied to these regions to prevent infection and/or to reduce the odor associated with such wounds. In more detail, a bacteria static material that is activated by moisture (such a silver nylon material made by Omishield, Sacuoito, or Swift) may be applied on the inner surfaces of the front and rear pads, support frame member, arm cuff, etc. (the inner surfaces being defined as the surfaces which contact the skin). The bacteria static material kills unwanted organisms and other odor causing organisms. Another bacteria static material which may be applied to areas on the shoulder brace is one manufactured by Becker Technology Group under the Trademark SILVERAPLPHA. The inventor of the present application has filed several related bacteria static material applications related to preventing odor and unwanted organisms using bacteria static materials such as silver-impregnated fabric.

In addition, it may be preferable to apply the bacteria static material only on certain portions of the front and rear pressure pads (and other skin touching areas on the shoulder brace). That is, there is a thermoplastic material provided on parts of the shoulder brace (e.g., the front and rear pads), which provide location stability for the front and rear pads (e.g., the front and rear pads do not slip due to the thermoplastic material). However, if a bacteria static material is applied to the entire inner surface of the front and rear pressure pads, for example, the pads may be more likely to slip. Therefore, it may be preferable to apply the bacteria static material only to the inner or outer regions of the pressure pads (i.e., to effectively utilize the location stability of the thermoplastic material as well as the benefits of the bacteria static material).

In addition, the present inventor has determined the amount of pressure to be applied to the shoulder joint to avoid the shoulder from popping out of its joint is in the range of about 1 to 40 pounds. This can be accomplished by measuring (via a pressure gauge including a spring loaded mechanism,), a minimum amount of pressure required to prevent an individual from dislocating his shoulder. In fact, many patients are referred to as "voluntary sublexers," which means they can voluntarily dislocate their shoulder. Based on preliminary investigations, it is believed the minimum pressure is about 1 pound (the pressure required to prevent a voluntary sublexerfrom discloting his shoulder). Further, it is believed a maximum amount of pressure is about 40 pounds.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A shoulder brace comprising: front and rear pressure pads to be respectively positioned on front and rear portions of an individual's shoulder joint; a support member to be positioned at a mid-section of the individual; a front frame member connected to the support member and the front pressure pad; a rear frame member connected to the support member and the rear pressure pad; an arm cuff to be positioned on the arm of the individual; and a compression mechanism configured to compress the front and rear frame members in accordance with a movement of the individual's arm such that the front and rear pressure pads press against the individual's shoulder joint, wherein the compression mechanism comprises: a gear box connected to the support member; a cord which is routed from an anchor point on the arm cuff, through the gear box, onto a surface of the rear frame member, over the individual's shoulder, and to an anchor point on the front frame member.

2. The shoulder brace according to claim 1, wherein the compression mechanism comprises: a gear box connected to the support member; a cord which is routed from an anchor point on the arm cuff, through the gear box, onto a pulley included on the rear frame member, under the individual's shoulder, to a pulley included on the front frame member, and back under the individual's shoulder to an anchor point on the rear frame member.

3. The shoulder brace according to claim 1, wherein the compression mechanism comprises: a gear box connected to the support member; a cord which is routed from an anchor point on the arm cuff, through the gear box, onto a surface of the rear frame member, under the individual's shoulder, to a pulley included on the front frame member, and back under the individual's shoulder to an anchor point on the rear frame member.

4. The shoulder brace according to claims 1, 2, or 3, further comprising: a plurality of pulleys positioned along the route of the cord so as to facilitate the movement of the cord.

5. The shoulder brace according to claims 1, 2, or 3, wherein the gear box includes a first wheel and a second wheel attached to the first wheel, said second wheel having a larger diameter than a diameter of the first wheel, and wherein the cord is wound around the first and second wheels at least once.

6. The shoulder brace according to claims 1 or 4, wherein the rear frame member comprises a groove configured to receive and route the cord along the surface of the rear frame member.

7. The shoulder brace according to claims 1, 2, or 3, wherein the cord comprises a braided cord having sufficient strength to compress the front and rear frame members in accordance with the movement of the individual's arm.

8. The shoulder brace according to claim 1, wherein the front pressure pad is movably connected to the front frame member and the rear pressure pad is fixed to the rear frame member.

9. The shoulder brace according to claim 1, wherein the support member is made from a semi-rigid material, the front and rear frame members are made from a rigid-material, and the front and rear pads and the arm cuff are made from a semi-rigid material having a thermoplastic padding to provide comfort and to provide location stability of the front and rear pads.

10. The shoulder brace according to claim 1, wherein the front frame member is pivotally connected to the support frame member at an end thereof, and is fixed in place via an anchor provided on the support frame member.

11. The shoulder brace according to claim 1, further comprising: an anchoring mechanism configured to secure the support frame member on the mid-section of the individual.

12. A shoulder brace comprising: front and rear pressure pads to be respectively positioned on front and rear portions of an individual's shoulder joint; a support member to be positioned at a mid-section of the individual; a front frame member connected to the support member and the front pressure pad; a rear frame member connected to the support member and the rear pressure pad; an arm cuff to be positioned on the arm of the individual; compression means for compressing the front and rear frame members in accordance with a movement of the individual's arm such that the front and rear pressure pads press against the individual's shoulder joint; and means for facilitating the movement of a cord included in the compression means, wherein the rear frame member comprises means for receiving and routing the cord along the surface of the rear frame member.

13. A shoulder brace comprising: front and rear pressure pads to be respectively positioned on front and rear portions of an individual's shoulder joint; a support member to be positioned at a mid-section of the individual; a front frame member connected to the support member and the front pressure pad; a rear frame member connected to the support member and the rear pressure pad; an arm cuff to be positioned on the arm of the individual; and compression means for compressing the front and rear frame members in accordance with a movement of the individual's arm such that the front and rear pressure pads press against the individual's shoulder joint, wherein the front pressure pad is movably connected to the front frame member and the rear pressure pad is fixed to the rear frame member.

14. A method of treating a shoulder injury via a shoulder brace including front and rear pressure pads; a support member; a front frame member connected to the support member and the front pressure pad; a rear frame member connected to the support member and the rear pressure pad; an arm cuff; and a compression mechanism, and said method comprising: positioning the front and rear pressure pads on front and rear portions of the individual's shoulder joint; positioning the support member at a mid-section of the individual; and positioning the arm cuff on the arm of the individual, wherein the compression mechanism compresses the front and rear frame members in accordance with a movement of the individual's arm such that the front and rear pressure pads press against the individual's shoulder joint, further comprising: determining, prior to positioning the shoulder brace on the individual, the amount of pressure the compression mechanism will press the front and rear pressure pads against the individual's shoulder joint.

* * * * *

UNITED STATES PATENT AND TRADEMARK OFFICE
Certificate

Patent No. 7,135,005 B2

Patented: November 14, 2006

On petition requesting issuance of a certificate for correction of inventorship pursuant to 35 U.S.C. 256, it has been found that the above identified patent, through error and without any deceptive intent, improperly sets forth the inventorship.
 Accordingly, it is hereby certified that the correct inventorship of this patent is: Bruce G. Kania, Bozeman, MT (US); Warren Harding, Cincinnati, OH (US); and David L. Zimmerman, Pony, MT (US).

Signed and Sealed this Sixth Day of May 2014.

*PATRICIA BIANCO*
*Supervisory Patent Examiner*
*Art Unit 3772*
*Technology Center 3700*